United States Patent
Goldfarb et al.

(10) Patent No.: US 11,759,624 B2
(45) Date of Patent: *Sep. 19, 2023

(54) SYSTEMS, APPARATUS, AND METHODS FOR DELIVERY OF THERAPEUTIC SUBSTANCE TO NASAL CAVITY

(71) Applicant: TUSKER MEDICAL, INC., Menlo Park, CA (US)

(72) Inventors: Eric Goldfarb, Belmont, CA (US); Rohit Girotra, San Francisco, CA (US); Mahyar Z. Kermani, San Ramon, CA (US)

(73) Assignee: Tusker Medical, Inc., Menlo Park, CA (US)

(*) Notice: Subject to any disclaimer, the term of this patent is extended or adjusted under 35 U.S.C. 154(b) by 193 days.

This patent is subject to a terminal disclaimer.

(21) Appl. No.: 17/183,939

(22) Filed: Feb. 24, 2021

(65) Prior Publication Data
US 2021/0178148 A1   Jun. 17, 2021

Related U.S. Application Data

(63) Continuation of application No. 16/754,236, filed as application No. PCT/US2018/058138 on Oct. 30, 2018.
(Continued)

(51) Int. Cl.
*A61N 1/04* (2006.01)
*A61K 9/00* (2006.01)
(Continued)

(52) U.S. Cl.
CPC .......... *A61N 1/0448* (2013.01); *A61K 9/0009* (2013.01); *A61K 9/0043* (2013.01);
(Continued)

(58) Field of Classification Search
CPC .. A61N 1/0448; A61N 1/0436; A61N 1/0546; A61N 1/306; A61K 9/0043
See application file for complete search history.

(56) References Cited

U.S. PATENT DOCUMENTS 5,505,715 A   4/1996   Shah et al.
6,139,861 A   10/2000  Friedman
(Continued)

FOREIGN PATENT DOCUMENTS

EP   1059097   12/2000

OTHER PUBLICATIONS

International Search Report and Written Opinion dated Aug. 8, 2022 for International Application No. PCT/US2022/024447, 13 pages.
(Continued)

*Primary Examiner* — Mallika D Fairchild
(74) *Attorney, Agent, or Firm* — Dickinson Wright PLLC

(57) ABSTRACT

Systems, apparatus, and methods are described for delivering a therapeutic substance to a target area within or proximate to a nasal cavity of a subject, including a reservoir configured to contain the therapeutic substance and a delivery interface by which the therapeutic substance is delivered to the target area. In some embodiments, systems, apparatus, and methods described herein can deliver a therapeutic substance using iontophoresis and/or electroosmosis.

21 Claims, 19 Drawing Sheets

Related U.S. Application Data

(60) Provisional application No. 62/579,243, filed on Oct. 31, 2017.

(51) Int. Cl.
 *A61N 1/05* (2006.01)
 *A61N 1/30* (2006.01)

(52) U.S. Cl.
 CPC ......... *A61N 1/0436* (2013.01); *A61N 1/0546* (2013.01); *A61N 1/306* (2013.01)

(56) References Cited

U.S. PATENT DOCUMENTS

| | | |
|---|---|---|
| 8,192,420 B2 | 6/2012 | Morriss et al. |
| 8,652,522 B2 | 2/2014 | Hasui et al. |
| 9,308,361 B2 | 4/2016 | Muni et al. |
| 9,364,648 B2 | 6/2016 | Girotra et al. |
| 9,421,356 B2 | 8/2016 | Anderson et al. |
| 9,492,661 B2 | 11/2016 | Lerner |
| 10,098,895 B2 | 10/2018 | Chang et al. |
| 2002/0068080 A1 | 6/2002 | Lerner |
| 2003/0133877 A1 | 7/2003 | Levin |
| 2005/0271725 A1 | 12/2005 | Kuribayashi et al. |
| 2008/0015540 A1 | 1/2008 | Muni et al. |
| 2009/0306579 A1 | 12/2009 | Jaffe et al. |
| 2010/0082088 A1 | 4/2010 | Fassih et al. |
| 2010/0331760 A1 | 12/2010 | Atanososka et al. |
| 2013/0174849 A1 | 7/2013 | Atkinson et al. |
| 2013/0217796 A1 | 8/2013 | Taylor et al. |
| 2013/0217798 A1 | 8/2013 | Sorrell et al. |
| 2013/0245608 A1* | 9/2013 | Muni .................... A61M 29/02 604/285 |
| 2014/0012182 A1 | 1/2014 | Shantha |
| 2014/0243793 A1* | 8/2014 | Morriss ................. A61M 15/08 604/514 |
| 2014/0276352 A1 | 9/2014 | Kermani et al. |
| 2016/0158051 A1 | 6/2016 | Mische |
| 2016/0193404 A1 | 7/2016 | Abel et al. |
| 2016/0278957 A1 | 9/2016 | Gaur et al. |
| 2020/0276434 A1 | 9/2020 | Goldfarb et al. |

OTHER PUBLICATIONS

European Application No. 18873691.2 Search Report dated Jul. 15, 2021.

International Search Report and Written Opinion dated Jan. 15, 2019 for PCT Application No. PCT/US2018/058138 filed Oct. 30, 2018; 9 pages.

Chinese Application No. 2018800648025 Text Of The Second Office Action.

* cited by examiner

SYSTEMS, APPARATUS, AND METHODS FOR DELIVERY OF THERAPEUTIC SUBSTANCE TO NASAL CAVITY

CROSS-REFERENCE TO RELATED APPLICATIONS

This Application is a continuation of U.S. patent application Ser. No. 16/754,236, filed Apr. 7, 2020, which was the U.S. National Phase Entry of PCT Application Serial No. PCT/US2018/058138, filed Oct. 30, 2018, which claims priority to and the benefit of U.S. Provisional Patent Application No. 62/579,243, filed Oct. 31, 2017. Each of these patent applications is titled "SYSTEMS, APPARATUS, AND METHODS FOR DELIVERY OF THERAPEUTIC SUBSTANCE TO NASAL CAVITY," and all of these patent applications are incorporated herein by reference in their entirety.

TECHNICAL FIELD

The present disclosure relates generally to systems, apparatus, and methods for delivering a substance to a nasal cavity or surrounding regions of a subject. More specifically, the present disclosure relates to systems, apparatus, and methods for accessing and delivering a therapeutic substance, such as an anesthetic, to a region within or proximate to a nasal cavity.

BACKGROUND

The nasal cavity forms a part of a subject's respiratory system. As shown in FIG. 1, the nasal cavity is an air-filled space disposed behind an exterior portion of the nose. Four pairs of sinuses are disposed around the nasal cavity, including the ethmoid sinuses, the maxillary sinuses, the frontal sinuses, and the sphenoid sinuses. The ethmoid sinuses are located in the ethmoid bone, which separates the nasal cavity from the brain, the maxillary sinuses are located behind the cheekbones near the maxillae or upper jaws, the frontal sinuses are located in the center of the frontal bone or forehead above each eye, and the sphenoid sinuses are located in the sphenoid bone near the optic nerve and the pituitary gland.

The nasal cavity is divided by a vertical partition, the nasal septum, into a right and a left side. Both sides of the nasal cavity are hollow and normally filled with air. The nasal cavity is exposed to the atmosphere of the outside environment via the anterior nares of the nose, as shown in FIG. 1. The anterior nares allow for the inhalation and exhalation of air through the nasal cavity. The nasal cavity is bounded by sidewalls, which include three pairs of turbinates or nasal concha—the inferior turbinates, the middle turbinates, and the superior turbinates. The turbinates project into the nasal cavity and divide the nasal passage of the nasal cavity into four groove-like air passages. As shown in FIG. 1, the inferior turbinates are disposed below the middle turbinates and the superior turbinates on the septum, the middle turbinates are disposed between the inferior turbinates and the superior turbinates, and the superior turbinates are disposed above the middle turbinates and the inferior turbinates. The turbinates are responsible for regulating airflow during inhalation.

The nasal cavity opens into the nasopharynx, which forms the upper part of the pharynx or throat. The nasopharynx contains a collection of lymphoid tissue towards the midline known as adenoids. The nasopharynx also includes a Eustachian tube opening, which connects the nasopharynx to the middle ear via the Eustachian tube. The Eustachian tube serves as an air channel between the middle ear and the nasopharynx that helps fill the middle ear with air and equalize the air pressure of the middle ear with the atmosphere.

The nasal cavity and the sinuses are lined with tissue known as mucosa that produces mucus. The mucus-covered surfaces of the nasal cavity help filter, humidify, and warm or cool air that is inhaled by a subject. The mucus-covered surfaces also trap harmful particles such as allergens or bacteria. The nasal cavity and its surrounding tissue, however, can become inflamed, infected, or obstructed. To treat these conditions, a physician may need to deliver therapeutic substances to the nasal cavity or its surrounding tissue. For example, a physician can deliver a therapeutic substance such as an anesthetic to tissue surrounding or proximate to the nasal cavity to alleviate pain or other discomfort during a surgical operation (e.g., a skull-based surgery, septoplasty, dental surgery, etc.). The physician can also delivery other therapeutic substances (e.g., analgesics, anti-inflammatories, antibiotics, antivirals, antifungals, antiparasitics, decongestants, mucokinetics, antihistamines, antioxidants, immunosuppressive agents, dissociatives, steroids, sedatives or hypnotics, anticholinergics, antiemetics, antiepiletics) to reduce or treat inflammation, infection, congestion, pressure, and/or other conditions within the nasal cavity and/or other conditions of a patient's body.

Delivery of therapeutic substances, including anesthetics, to the nasal cavity or surrounding tissue regions can be used to treat and/or aid in treatment of allergic or non-allergic rhinitis, nasal obstruction (e.g., an obstruction caused by sinusitis, allergies, etc. or an anatomical factor such as a deviated septum, enlarged adenoids, nasal polyps, foreign objects, turbinate hypertrophy, nasal valve collapse, etc.), nasal polyps, sinusitis (e.g., ostium, intra-sinus, post-sinus surgery), epistaxis, allergies, migraines, and tinnitus, polyposis, etc. Oftentimes, the therapeutic substance may need to be maintained against a tissue surface for an extended period of time to provide effective results. For example, for treating inflammation or applying an anesthetic, a therapeutic substance may need to be applied to a tissue surface within the nasal cavity for a sufficient period of time such that the therapeutic substance can diffuse or perfuse through the surface into the tissue. Additional apparatuses and methods for delivering a therapeutic substance to the nasal cavity or surrounding tissue are desirable.

SUMMARY

Systems, apparatus, and methods are described for delivering a therapeutic substance to a nasal cavity and/or surrounding tissue regions of a subject. The delivery system preferably provides soft, non-painful contact with the nasal cavity and/or surrounding tissue. In some embodiments, the therapeutic substance may be an anesthetic, such as lidocaine, which may be used to anesthetize the nasal cavity or its surrounding tissue in preparation for a surgical operation. The delivery system and method can enable delivery of the therapeutic substance over a sufficient time to deliver a therapeutically effective dose, without requiring the subject to be still and/or to maintain an awkward head position or orientation, e.g. with their head tilted to allow drops of liquid therapeutic substance to be maintained in position against a tissue surface. In some embodiments, the therapeutic substance can be an anti-hemorrhagic or hemostatic agent, such as an anti-fibrinolytic acid, that reduces bleeding during or after a surgical procedure. The therapeutic substance can be delivered before, during, and/or after a surgical procedure to improve surgical visualization and avoid nasal packing. In some embodiments, the therapeutic substance can be an analgesic, an anti-inflammatory, an antibiotic, an antiviral, an antifungal, an antiparasitic, a decongestant, a mucokinetic, an antihistamine, an antioxidant, an immunosuppressive agent, an dissociative, a steroid, a sedative or hypnotic, an anticholinergic, an antiemetic, an antiepiletic, etc. or any combination of therapeutic substances.

In some embodiments, systems and methods described herein can deliver a therapeutic substance to a nasal cavity and/or surrounding tissue regions of a subject using iontophoresis. With iontophoresis, a low-level electric current can be applied to a charged solution (i.e., an iontophoresis fluid) to transport ions of a therapeutic substance (e.g., an anesthetic, an analgesic, an anti-inflammatory, an antibiotic, an antiviral, an antifungal, an antiparasitic, a decongestant, a mucokinetic, an antihistamine, an antioxidant, an immunosuppressive agent, an dissociative, a steroid, a sedative or hypnotic, an anticholinergic, an antiemetic, an antiepiletic, etc.) across skin or other tissue surfaces into the surrounding tissue. The delivery system and method can be configured to maintain an iontophoresis fluid against a tissue surface and to apply an electric current to the fluid to drive delivery of a therapeutic substance in the iontophoresis fluid through the tissue surface. The delivery system and method can include an electrode device that is in fluid communication with the iontophoresis fluid such that an electric current can be supplied to the fluid to perform the iontophoresis procedure.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Figure 1:
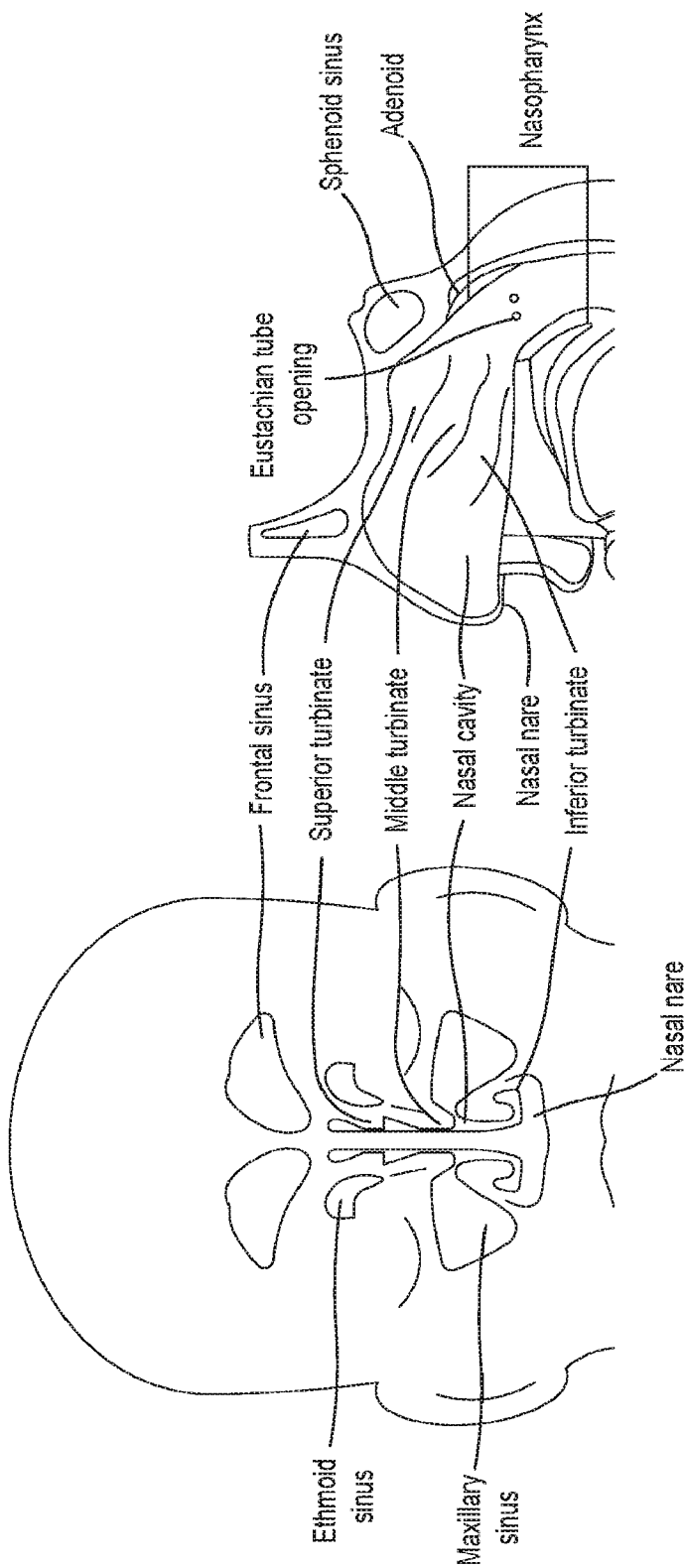
FIG. 1 illustrates the anatomy of a nasal cavity and surrounding regions.

Systems, apparatus, and methods are described herein for delivery of therapeutic substances to the nasal cavity and/or surrounding tissue areas. As illustrated schematically in FIG. 2, a delivery system 100 can deliver a therapeutic substance TS to a target area TA in a nasal cavity NC of a subject. Although target area TA is shown as being disposed within nasal cavity NC, in other embodiments, target area TA can be disposed outside of the nasal cavity NC (e.g., target area TA can be proximate to or adjacent to the nasal cavity NC).

Delivery system 100 can be an example of a passive delivery system in which a therapeutic substance TS is allowed to elute, diffuse, or otherwise be passively released into a target area TA. Delivery system 100 can include a reservoir 110 that can contain therapeutic substance TS. A delivery interface 120 can be part of, or coupled fluidically to, reservoir 110, enabling therapeutic substance TS to contact, and enter (e.g., via diffusion), target area TA. Optionally, an inlet 130 can be coupled fluidically to reservoir 110, enabling reservoir 110 to be filled, or refilled, with the therapeutic substance TS. Delivery system 100 can include a body or housing 140 that supports, or defines, reservoir 110, delivery interface 120, and/or inlet 130.

Delivery system 100 may also include a retrieval element 145 by which system 100 can be removed from the nasal cavity NC of the subject. Delivery system 100 may be deployed into an operative position in the nasal cavity NC of the subject with a deployment device 180, which may be releasably engaged with delivery system 100 in preparation for deployment of delivery system 100, and released from delivery system 100 after deployment in nasal cavity NC, or alternatively may remain engaged with delivery system 100 during delivery of therapeutic substance TS.

Each component of delivery system 100 can be implemented in various ways. Reservoir 110 may be formed by a solid structure within which therapeutic substance TS (in fluid and/or solid form) may be eluted, diffused, or released by other mechanisms. For example, reservoir 110 may be an open cell foam in which therapeutic substance TS in liquid form is contained and from which therapeutic substance TS may be released by osmotic diffusion from a distal surface of the foam reservoir that is in contact with the target area TA (the delivery interface 120). That is, delivery or release of therapeutic substance TS may be driven by a differential in concentration of therapeutic substance TS in the foam and in target area TA. The foam reservoir 110 may be delivered by mechanical insertion through the nasal cavity into operative apposition with the target area TA. As needed, therapeutic substance TS may be added to reservoir 110 by supplying it, e.g. in liquid form, to a proximal surface of the foam, serving as inlet 130.

In another embodiment, reservoir 110 may be in the form of a solid structure that biodegrades, i.e. formed of a material that breaks down in contact with tissue, and can release therapeutic substance TS as reservoir 110 biodegrades. In some embodiments, reservoir 110 can be formed of a structure that degrades based on exposure to environmental conditions associated with the nasal cavity NC. For example, reservoir 110 can degrade in response to being subjected to a certain temperature for a predefined period of time. Alternatively or additionally, reservoir 110 can degrade in response to application of pressure (e.g., a user pressing on an outside surface of the nose such that pressure is applied to the reservoir 110 disposed inside the nose), a change in pressure (e.g., based on a user inhaling and/or exhaling), and moisture level associated with air within the nasal cavity and/or a tissue surface, etc. Reservoir 110 can be configured to maintain apposition between delivery interface 120 and target area TA (or a tissue surface above target area TA) until a therapeutically effective amount or dose of therapeutic substance TS has been delivered to the target area TA. Accordingly, reservoir 110 can be configured to degrade over a period of time that enables the delivery interface 120 to be maintained against the target area TA for a sufficient amount of time to enable a therapeutically effective amount of therapeutic substance TS to be delivered to the target area TA.

In other embodiments, reservoir 110 may be formed of a carrier material in which therapeutic substance TS in liquid form is mixed, or in solid, particulate form is dissolved, suspended, etc. The carrier material and therapeutic substance TS may be delivered through the nasal cavity NC into operative apposition with target area TA, for example by injection, spray, or other suitable delivery mechanism. Thus, reservoir 110 may be formed in situ on target area TA. The carrier material and therapeutic substance may be delivered as a foam or mousse or a hydrogel. In another embodiment, the carrier may be deliverable in a liquid form that changes to a solid form, e.g. by a change in temperature. Such carriers are known from applications such as liquid bandages. In this embodiment, the carrier, containing therapeutic substance TS, may be injected or sprayed in liquid form against the surface of target area TA and then solidify due to the higher temperature of nasal cavity NC, thus forming reservoir 110 in situ on target area TA.

In another embodiment, reservoir 110 may be in the form of a stable/solid thin film that may contain therapeutic substance TS as with the other embodiments described above, and the therapeutic substance TS may be delivered to target area TA by diffusion when the thin film is in apposition with target area TA. Alternatively, the thin film may function as a body 140 on which a reservoir 110 in the form of a foam, hydrogel or other material containing therapeutic substance TS may be carried. In other words, the body 140 may be a thin film substrate, and reservoir 110 may be a layer of material disposed on the distal surface of the body 140.

In another embodiment, reservoir 110 may be in the form of a bundle or other mass of wicking, fibrous material, i.e. a material that can absorb therapeutic substance TS in liquid form, and conduct therapeutic substance TS by capillary action through the body of reservoir 110 to a distal surface of reservoir 110 in contact with target area TA, from which the therapeutic substance TS can diffuse into target area TA. As needed, therapeutic substance TS may be added to reservoir 110 by supplying it, e.g. in liquid form, to a proximal surface or end of the wicking material, serving as inlet 130.

In some embodiments, including those described above, reservoir 110 can be configured to deform, e.g., change configuration and/or shape, once reservoir 110 is disposed within the nasal cavity NC. For example, as depicted in FIGS. 6A-12B (further described below), a reservoir can be formed of a material that changes shape such that a delivery interface associated with the reservoir conforms to a shape of a tissue surface. Stated differently, a reservoir can be a deformable structure that includes a delivery interface capable of deforming to conform to a shape of a tissue surface.

Figure 2:
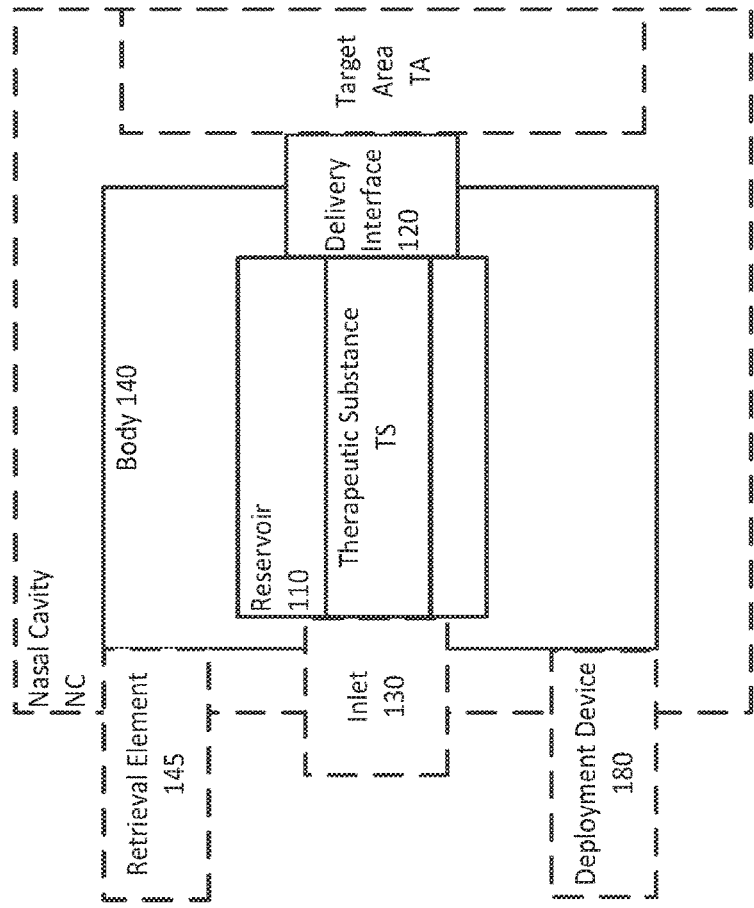
FIG. 2 is a schematic illustration of a therapeutic delivery system according to some embodiments.

Although, in the embodiment depicted in FIG. 2, delivery system 100 has one delivery interface 120 that can contact and deliver therapeutic substance TS to one target area TA, in other embodiments, delivery system 100 can have multiple delivery interfaces 120 that enable therapeutic substance TS to contact, and enter, multiple target areas TA. In some embodiments, delivery system 100 can deliver therapeutic substance TS to multiple target areas TA simultaneously.

Figure 3:
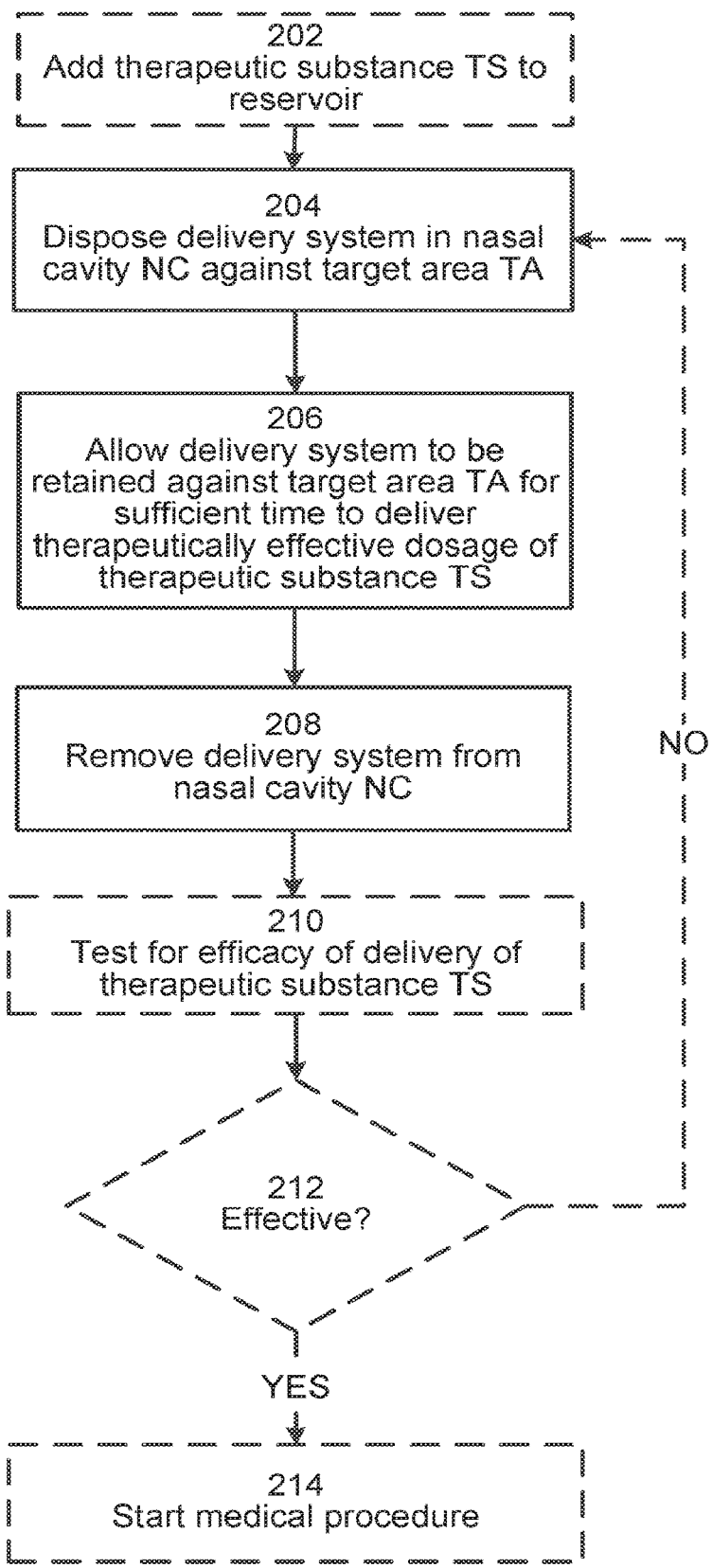
FIG. 3 is a flow diagram illustrating a method for delivering a therapeutic substance to a target area in a nasal cavity of a subject in accordance with some embodiments.

A method 200 of delivering therapeutic substance TS to target area TA in nasal cavity NC is illustrated schematically in FIG. 3.

Initially, therapeutic substance TS may be added to the reservoir, such as reservoir 110 described above, in step 202. In step 204, a delivery system, such as delivery system 100 disclosed above, is deployed in nasal cavity NC of the subject. In particular, deployment includes disposing the delivery system with its delivery interface, such as delivery interface 120, in operative apposition with target area TA within nasal cavity NC of the subject. In step 206, the delivery system is allowed to be retained in nasal cavity NC of the subject for sufficient time to deliver a therapeutically effective dosage of the therapeutic substance TS to target area TA of the subject. In step 208, the delivery system is removed from nasal cavity NC of the subject.

Optionally, in step 210, a test may be conducted to evaluate the efficacy of the delivery of therapeutic substance TS. For example, if therapeutic substance TS is an anesthetic, the therapeutically effective dosage to be delivered to target area TA of the subject may be the dosage required to anesthetize target area TA so that a medical procedure may performed, such as a surgery to tissue or bone within nasal cavity NC. The efficacy of delivery of the therapeutic substance TS may thus be a test of anesthetization of target area TA, e.g. by touching target area TA and assessing the subject's response. In step 212, if it is determined that the delivery was not effective, the method may revert to step 204 to dispose the, or another, delivery system in nasal cavity NC to deliver more therapeutic substance TS. Alternatively, if it is determined that the delivery was effective, the method may proceed to step 214, in which a medical procedure, such as a surgical operation, may be started. In another embodiment, therapeutic substance TS can be an antihistamine, a steroid, and/or an antibiotic used to treat an allergy or an infection within nasal cavity NC. The therapeutically effective dosage to be delivered to target area TA of the subject may be a dosage required to treat the condition, and the efficacy of delivery can be tested by examining target area TA and/or evaluating symptoms that are commonly associated with the condition (e.g., inflammation, congestion, nasal discharge, pain, bleeding, sneezing, itching, etc.). In step 212, if it is determined that the delivery was not effective, then the method may revert to step 204 to apply additional therapeutic substance TS to target area TA. Alternatively, if it is determined that the delivery was effective, then the method can terminate without proceeding to step 214 or, optionally, the method can proceed to step 214, where another medical procedure can be started. For example, if a delivery system is being used by a subject at home or otherwise outside of a medical facility, the subject can test, at step 210, the efficacy of the delivery of therapeutic substance TS by evaluating whether certain symptoms of a nasal condition (e.g., inflammation, congestion, nasal discharge, pain, bleeding, sneezing, itching, etc.) remain after removing the delivery system. And at step 212, if it is determined that the delivery was not effective, the subject can place the delivery system or another delivery system back in the subject's nasal cavity to apply additional therapeutic substance TS to target area TA. Alternatively, if it is determined that the delivery was effective, method 200 can terminate.

Therapeutic substance TS can be any suitable substance or combination of substances, in any suitable dosage form or combination of dosage forms. Non-limiting examples include analgesics (e.g., non-steroidal anti-inflammatory drugs (NSAIDs) like acetaminophen, COX-2 inhibitors, opioids, flupirtine, cannabinoids, capsaicinoids, etc.), anesthetics (e.g. lidocaine, benzocaine, procaine, amethocaine, cocaine, tetracaine, prilocaine, bupivicaine, levobupivacaine, ropivacaine, mepivacaine, dibucaine, etidocaine, etc.), anti-inflammatories (e.g. NSAIDs like aspirin, ibuprofen, and naproxen, peptides, steroids or glucocorticosteroids like dexamethasone, etc.), antibiotics (e.g., ciprofloxacin, ciprofloxacin otic suspension, amoxicillin, amoxicillin-clavulanate, beta lactamase inhibitor, etc.), antivirals, antifungals, antiparasitics, decongestants (e.g., ephedrine, levomethamphetamine, naphazoline, oxymetazoline, phenylephrine, phenylpropanolamine, propylhexedrine, synephrine, tetrahydrozoline, xylometazoline, pseudoephedrine, tramazoline, etc.), mucokinetics (e.g., mucolytics like acetylcysteine, expectorants like guaifenesin, surfactants, etc.), antihistamines, antioxidants, immunosuppressive agents, and dissociatives (e.g., NMDA receptor antagonists like gacyclidine, κ-opioid receptor agonists, etc.). Suitable dosage form(s) can include liquids (including solutions, suspensions, and colloids) delivered (e.g., sprayed) as a liquid, liquid aerosol, foam, emulsion, sol, etc.; gases (including solutions, suspensions, and colloids) delivered as a vapor; and solids (including solutions, suspensions, and colloids) delivered as solid aerosols, solid foam, gel, sol, etc., including solids that are incorporated into or onto a solid or porous substrate for elution or release by biodegradation of the substrate. The therapeutic substance can include small molecules that can penetrate through mucosa, skin, or other tissue surfaces.

Suitable biodegradable solids may include, but are not limited to, agro-polymers, including polysaccharides and proteins, or biopolyesters including natural monomers (e.g., polyhydroxyalkanoates (PHAs) like poly-3-hydroxybutyrate (PHB), polyhydroxyvalerate (PHV) and polyhydroxyhexanoate (PHH), etc.), renewable monomers (e.g., polylactic acid (PLA)), and synthetic monomers (e.g., polybutylene succinate (PBS), polycaprolactone (PCL), etc.). Additional examples of biodegradable solids include polyglycolic acid, poly(lactic-co-glycolic) acid, poly-ε-caprolactone, polydioxanone, chitosan, hyaluronic acid, poly(2-hydroxyethyl-methacrylate), poly(ethylene glycol), polyurethanes, poly(ester amide)s, polyanhydrides, polyvinyl alcohol, cellulose esters, polyethylene terephthalate, and hydrogels. In some embodiments, a normal plastic polymer such as polyethylene or polypropylene may be incorporated with an additive which causes degradation (e.g., due to oxidation). Biodegradable materials may include films, fibers, extruded or molded products, laminates, foams, powders, nonwovens, adhesives, and/or coatings.

Figure 4A:
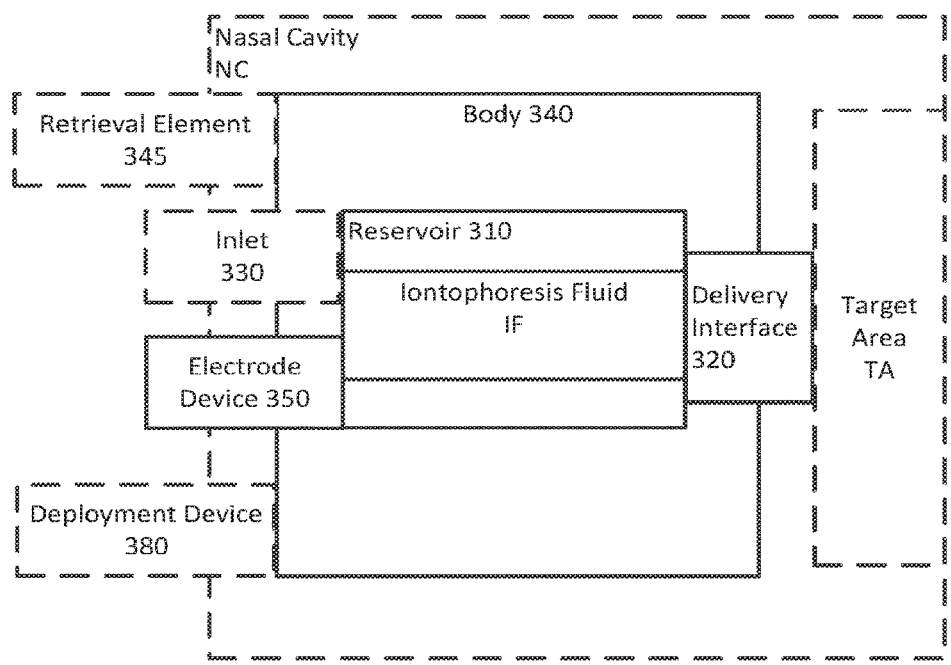
FIGS. 4A-4B are a schematic illustration of a therapeutic delivery system including an electrode device according to some embodiments.
Figure 4B:
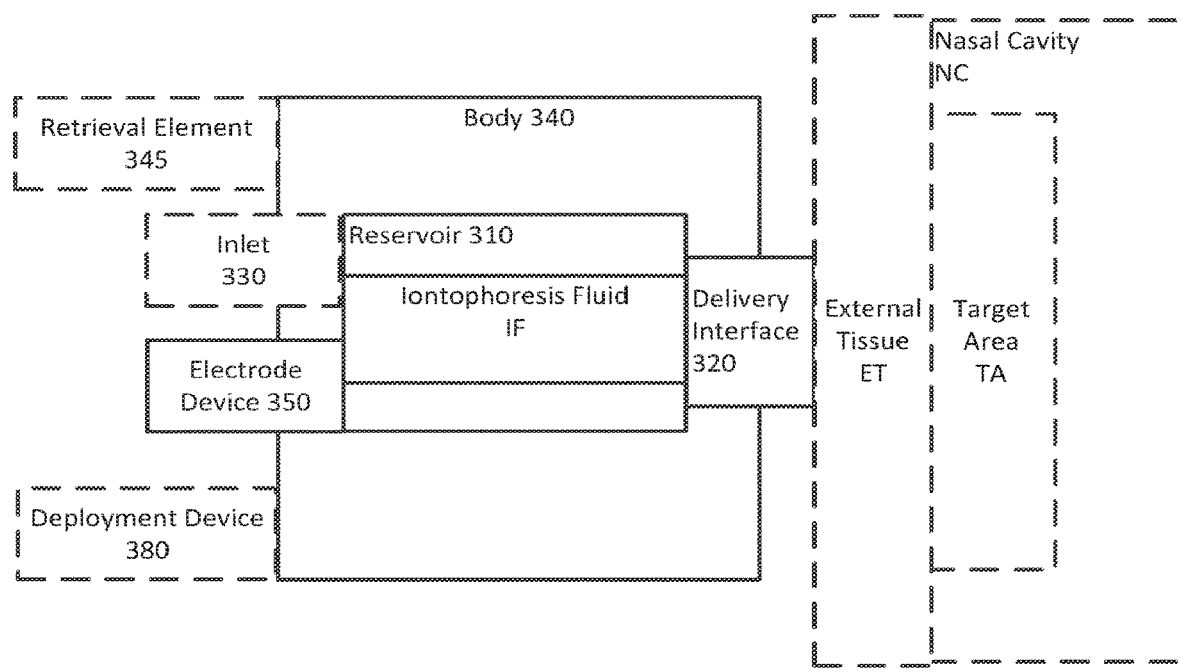

FIGS. 4A and 4B are schematic illustrations of a delivery system 300 according to another embodiment. Delivery system 300 can be an example of an active delivery system in which a therapeutic substance is driven via iontophoresis (e.g., using an electric current) into a target area TA.

Similar to delivery system 100, delivery system 300 can include a reservoir 310, a delivery interface 320, and a body 340. As illustrated in FIG. 4A, delivery system 300 can be disposed within a nasal cavity NC of a subject and be brought into operative apposition with a target area TA within nasal cavity NC. Alternatively, delivery system 300 can be positioned outside of nasal cavity NC (e.g., outside of the subject's nose) and be brought into operative apposition with external tissue ET (e.g., the external skin of a subject's nose) located proximate or adjacent to target area TA. Delivery system 300 can be configured to deliver a therapeutic substance to a single target area TA or to multiple target areas TA. For example, delivery system 300 can have multiple reservoirs 310 and delivery interfaces 320 such that delivery system 300 can deliver a therapeutic substance to multiple target areas TA within and/or proximal to nasal cavity NC at substantially the same time. In other embodiments, delivery system 300 can deliver a therapeutic substance to multiple target areas TA in a sequential manner.

Reservoir 310 can contain an iontophoresis fluid IF, including an ionic therapeutic substance that can be driven (e.g., transported) into tissue by applying an electric current to iontophoresis fluid IF. The iontophoresis fluid IF can contain the ionic therapeutic substance, e.g., iontophoresis fluid IF can be an ionic solution with ions of the therapeutic substance. The therapeutic substance can include small molecules that can penetrate through mucosa, skin, or other tissue surfaces. Iontophoresis can be used to deliver a wide range of relatively small molecules. For example, iontophoresis can be used to deliver anesthetics, anti-histamines, and anti-inflammatory drugs to target tissue. Examples of these molecules that have been successfully delivered via iontophoresis include lidocaine with a molecular weight of approximately 234 Da, epinephrine with a molecular weight of approximately 183 Da, anti-histamines with a molecular weight of approximately 380 Da, and steroids with a molecular weight of approximately 400-500 Da. Iontophoresis has also been used to deliver small ions such as lithium with a molecular weight of approximately 7 Da to target areas to treat gouty arthritis. Iontophoresis can also be used to enhance transdermal delivery of larger molecules such as insulin having a molecular weight of approximately 6000 Da. In some embodiments, iontophoresis fluid IF can also include a buffering solution for maintaining the pH of the iontophoresis fluid IF at biologically appropriate levels. In some embodiments, iontophoresis fluid IF can also include inactive ingredients suitable for nasal applications. In some embodiments, iontophoresis fluid IF can include more than one therapeutic substance.

Advantages of iontophoresis include quicker delivery rates and deeper local penetration of a therapeutic substance into surrounding tissue. For example, in certain applications, it may be desirable to have a therapeutic substance penetrate deeper into tissue such that the therapeutic substance can have an effect on nerve endings found in deeper tissue structures. Alternatively or additionally, it may be desirable to increase the rate of delivering a therapeutic substance into tissue, e.g., to produce a stronger and/or faster drug effect, to avoid breakdown of a drug delivery interface prior to effective drug delivery, etc. For example, when a delivery system and/or delivery interface is designed to break down over time (e.g., in the case of a degradable carrier material), iontophoresis can be used to increase drug uptake prior to breakdown of the delivery system and/or delivery interface.

Delivery interface 320 can be part of, or coupled fluidically to, reservoir 310, enabling iontophoresis fluid IF to come into contact with a tissue surface. Delivery interface 320 and/or reservoir 310 can be implemented in various ways, including, for example, a solid structure (e.g., a container or cup, a flexible bag, a sponge), a carrier material (e.g., a foam, a mousse, a hydrogel), a thin film or membrane, or a bundle or mass of fibrous material. Optionally, an inlet 330 can be coupled fluidically to reservoir 310, enabling reservoir 310 to be filled, or refilled, with iontophoresis fluid IF. Body 340 can support, or define, reservoir 310, delivery interface 320, and/or inlet 330. Delivery system 300 optionally can include a retrieval element 345 for removing delivery system 300 from nasal cavity NC and/or another location proximate to the nasal cavity NC and a deployment device 380 for deploying delivery system 300 in nasal cavity NC and/or another location proximate to the nasal cavity NC. In some embodiments, a single component or mechanism such as, for example, a flexible shaft, beam, bar, wire, etc. can serve as both retrieval element 345 and deployment device 380.

Delivery system 300 can include an electrode device 350 that is configured to apply an electric current to iontophoresis fluid IF to transport the therapeutic substance within iontophoresis fluid IF across the tissue surface into the surrounding tissue (e.g., target area TA, external tissue ET). Electrode device 350 can include a control unit for powering and controlling application of the electric current, an electrode for applying the electric current, and a return electrode for providing an electrical return path to the control unit. The electrode for applying the electric current can be positioned in contact with iontophoresis fluid IF, and the return electrode can be distanced from that electrode e.g., at a location on a patient's skin (e.g., back of neck, shoulder, etc.). In some embodiments, electrode device 350 can be coupled to and/or integrally formed with body 340 and/or reservoir 310. In other embodiments, electrode device 350 can be brought into engagement with reservoir 310 such that a tip (e.g., an electrode tip) of electrode device 350 is in contact with iontophoresis fluid IF and can apply an electric current to iontophoresis fluid IF. Electrode device 350 can be designed to deliver a low-level current such that patient discomfort is reduced. For example, electrode device 350 can include an electrode with a relatively large conductive surface that helps reduce current density. In some embodiments, electrode device 350 can deliver a current with a current profile that reduces discomfort during delivery. For example, the current profile can gradually ramp-up and/or ramp-down, or have an alternating profile (e.g., pulsed, sine-wave, etc.). In some embodiments, electrode device 350 can also include insulating components and/or portions (e.g., an insulating sheath or sleeve) that can surround parts of the conductive surface of the electrode and help direct current flow toward the tissue surface when in use. In some embodiments, electrode device 350 can have a portion that is flexible or malleable.

In some embodiments, iontophoresis systems and/or electrode devices described in U.S. Pat. No. 8,452,392 to Morriss, et al., entitled "Systems and methods for anesthetizing ear tissue," the disclosure of which is incorporated herein by reference, can be used and/or adapted for use in delivering a therapeutic substance to a subject's nasal cavity NC or surrounding tissue regions. For example, the dimensions, shape, or other configuration of an electrode device, such as electrode device 350 and/or electrode devices disclosed in U.S. Pat. No. 8,452,392, can be designed according to the anatomy of a subject's nasal cavity NC.

In some embodiments, electrode device 350 is configured to provide a direct current (DC) signal. For example, electrode device 350 can provide a constant current (e.g., approximately 1 mA) for a period of time. In some embodiments, electrode device 350 is configured to provide an alternating current (AC) signal with a DC offset. For example, a DC signal can be modulated by a circuit with an AC signal to produce a modulated current signal. The modulated current signal can be any one of a pulsed square waveform, a sinusoidal waveform, a sawtooth waveform, a trapezoidal waveform, etc. In some embodiments, electrode device 350 is configured to ramp up and/or ramp down the current. For example, electrode device 350 can gradually ramp up a constant current or a modulated current until the current reaches a predefined value (e.g., approximately 1 mA) and/or to gradually ramp down the current from a predefined value to zero. In some embodiments, current profiles such as those described in U.S. application Ser. No. 13/804,491, entitled "System and method for providing iontophoresis at tympanic membrane, published as U.S. Patent Publication No. 2014/0276352, the disclosure of which is incorporated herein by reference, can be used and/or adapted to deliver a therapeutic substance to a subject's nasal cavity NC or surrounding tissue regions.

Similar to delivery system 100, each component of delivery system 300 can be implemented in various ways. Reservoir 310 may be formed by a solid structure that contains iontophoresis fluid IF and provides an outlet (e.g., delivery interface 320) through which a therapeutic substance in iontophoresis fluid IF can be delivered to a tissue region (e.g., target area TA). For example, reservoir 310 may be an open cell foam in which iontophoresis fluid IF is contained and from which a therapeutic substance within iontophoresis fluid IF can be delivered via an iontophoresis procedure to a tissue region. That is, delivery of the therapeutic substance may be driven by an electric current that is applied to the iontophoresis fluid IF. The foam reservoir 310 may be delivered by mechanical insertion through nasal cavity NC into operative apposition with a tissue surface. As needed, iontophoresis fluid IF and/or therapeutic substance may be added to reservoir 310 by supplying it, e.g. in liquid form, to a proximal surface of the foam, serving as inlet 330.

In other embodiments, reservoir 310 may be formed of a carrier material (e.g., a foam, a mousse, a hydrogel) that contains iontophoresis fluid IF. For example, the carrier material can be saturated and/or mixed with iontophoresis fluid IF. In some embodiments, the carrier material can be electrically conductive, e.g. capable of conducting an electric current supplied from an electrode device, such as electrode device 350. The carrier material and iontophoresis fluid IF may be delivered through the nasal cavity into operative apposition with a tissue surface, for example, by injection, spray, or other suitable delivery mechanism. Thus, reservoir 310 may be formed in situ on a tissue surface. In some embodiments, the carrier may be deliverable in a liquid form that changes to a solid form (e.g., a solid porous material).

In other embodiments, reservoir 310 may be in the form of a thin film or membrane that contains iontophoresis fluid IF. The thin film or membrane can be electrically conductive, e.g. capable of conducting an electric current supplied from an electrode device, such as electrode device 350. The thin film or membrane can be placed in contact with or proximate to the electrode device. In some embodiments, the thin film or membrane can function as a body 320 on which a reservoir 310 in the form of a foam, hydrogel, or other material containing iontophoresis fluid IF may be carried.

In another embodiment, reservoir 310 may be in the form of a bundle or other mass of wicking, fibrous material, i.e. a material that can absorb iontophoresis fluid IF, and conduct iontophoresis fluid IF by capillary action through the body of reservoir 310 to a distal surface of reservoir 310 in contact with a tissue surface, from which a therapeutic substance within iontophoresis fluid IF can be delivered via an iontophoresis procedure into a tissue region. An electrode device (e.g., electrode device 350) can be placed in contact with the wicking, fibrous material to supply an electric current to the iontophoresis fluid IF to drive the therapeutic substance into the tissue region. As needed, iontophoresis fluid IF and/or therapeutic substance may be added to reservoir 310 by supplying it, e.g. in liquid form, to a proximal surface or end of the wicking material, serving as inlet 330.

Figure 5:
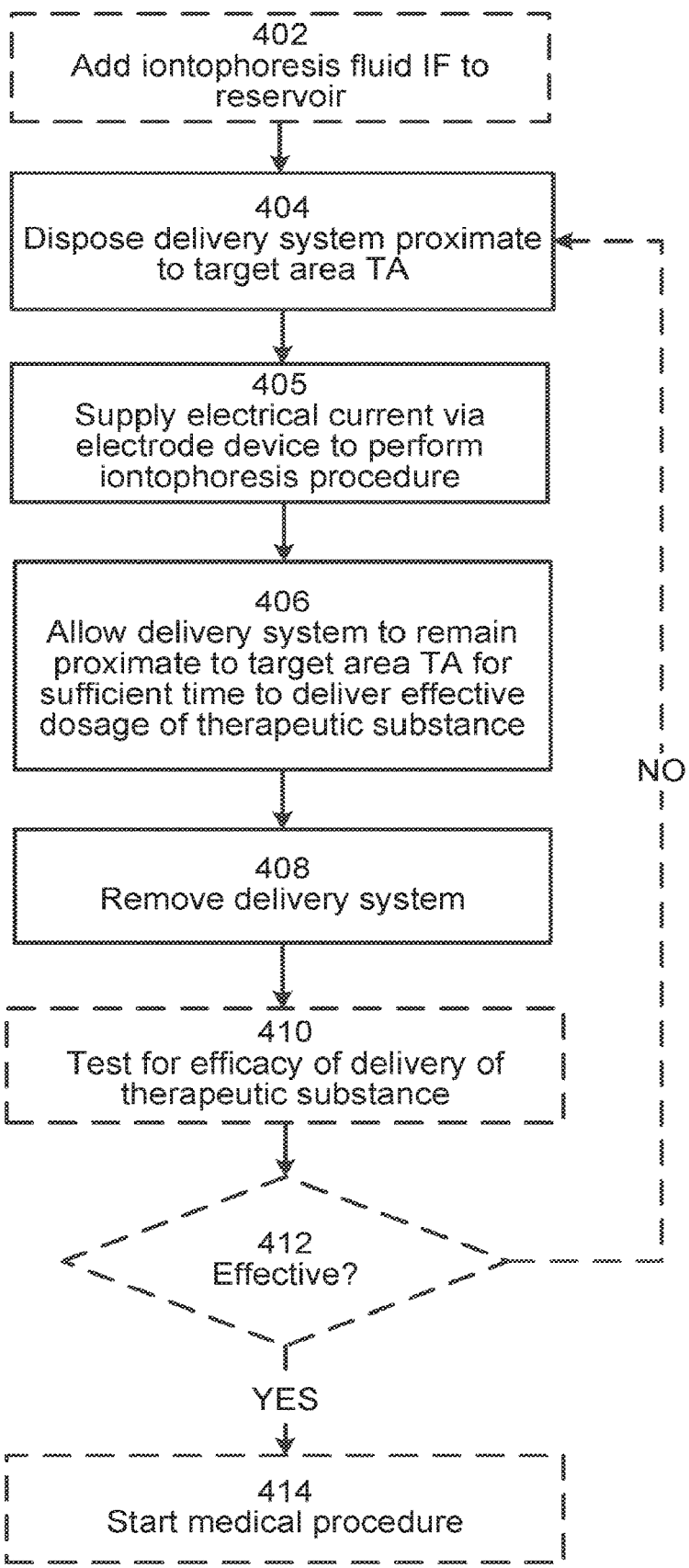
FIG. 5 is a flow diagram illustrating a method for delivering a therapeutic substance to a target area in a nasal cavity of a subject in accordance with some embodiments.

A method 400 of delivering a therapeutic substance via an iontophoresis procedure to a target area TA is illustrated schematically in FIG. 5. In step 402, iontophoresis fluid IF containing a therapeutic substance can be added to the reservoir, such as reservoir 310 described above. In step 404, a delivery system, such as delivery system 300 disclosed above, is disposed proximate or adjacent to a target area TA of the subject. For example, the delivery system can be disposed with its delivery interface, such as delivery interface 320, in operative apposition with target area TA of the subject. Alternatively, the delivery system can be disposed with its delivery interface in operative apposition with a tissue surface, such as external tissue ET. In particular, the delivery system can be disposed outside of a subject's nose but in operative apposition with an external skin surface of the nose and/or surrounding area (e.g., surrounding facial area).

In step 405, an electrode device, such as electrode device 350, can be used to deliver the therapeutic substance within iontophoresis fluid IF to target area TA using iontophoresis. For example, the electrode device can be brought into contact with the reservoir and/or iontophoresis fluid IF and used to supply a current to iontophoresis fluid IF to transport the therapeutic substance into target area TA. In step 406, the delivery system is allowed to be retained proximate to target area TA for sufficient time to deliver a therapeutically effective dosage of the therapeutic substance to target area TA of the subject. In step 408, the delivery system is removed, e.g. from nasal cavity NC or an area proximate to nasal cavity NC.

Similar to method 200 described above, method 400 may also include optional steps 410, 412, and 414. In step 410, a test may be conducted to evaluate the efficacy of the delivery of therapeutic substance. In step 412, if it is determined that the delivery was not effective, the method may revert to step 404 to dispose the, or another, delivery system proximate to target area TA to deliver more therapeutic substance to target area TA. Alternatively, if it is determined that the delivery was effective, the method may proceed to step 414, in which a medical procedure, such as a surgical operation, may be started. In some embodiments, similar to that described above with respect to method 200, where a therapeutic substance, such as, for example, an antihistamine, a steroid, and/or an antibiotic, is delivered to treat a condition in nasal cavity NC, the method 400 may terminate after step 412 when it is determined that the delivery of the therapeutic substance was effective.

In addition or alternatively, delivery systems described herein can be used to deliver a therapeutic substance via electroosmosis. For example, a delivery system (e.g., delivery system 300) can be used to deliver a therapeutic substance to target area TA via electroosmosis in addition to iontophoresis. The delivery system can include a reservoir (e.g., reservoir 310), which can contain a fluid including non-ionic molecules that can pass into target area TA via a concentration gradient. The delivery can occur under the influence of an electric field via the application of an electric current to the fluid, which can include an ionic component that delivers the applied electric current to a tissue membrane to open channels in the tissue membrane. After the channels in the tissue membrane are opened, the non-ionic drug molecules can be delivered to target area TA via a concentration gradient.

Various non-limiting, exemplary embodiments are described below.

Figure 6A:
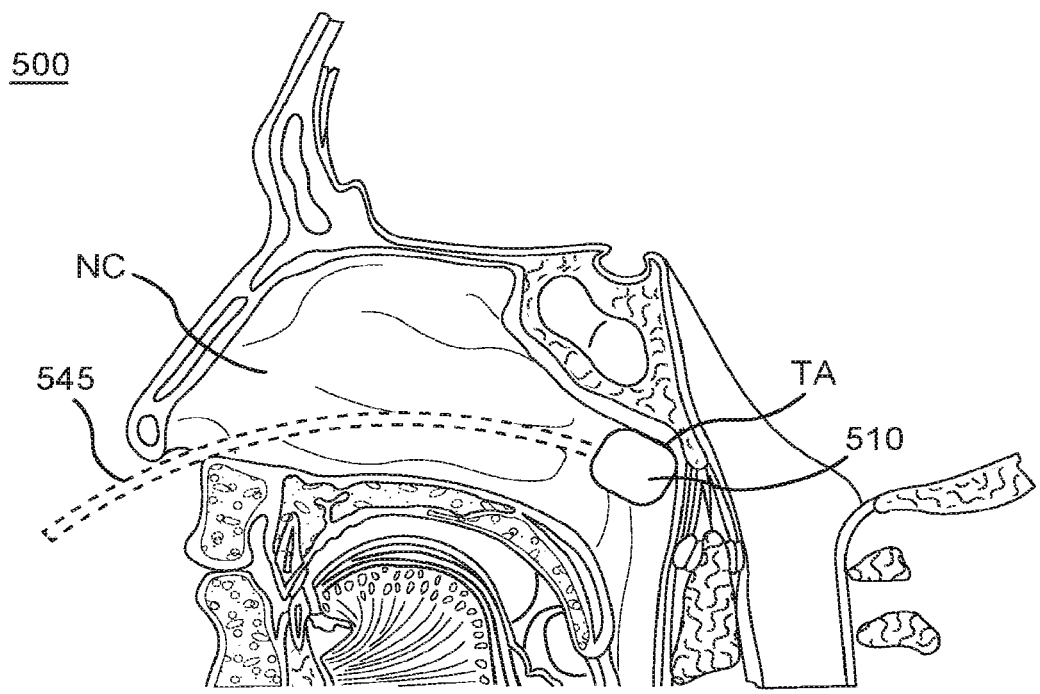
FIGS. 6A-6B are schematic illustrations of a therapeutic substance delivery system according to an embodiment.
Figure 6B:
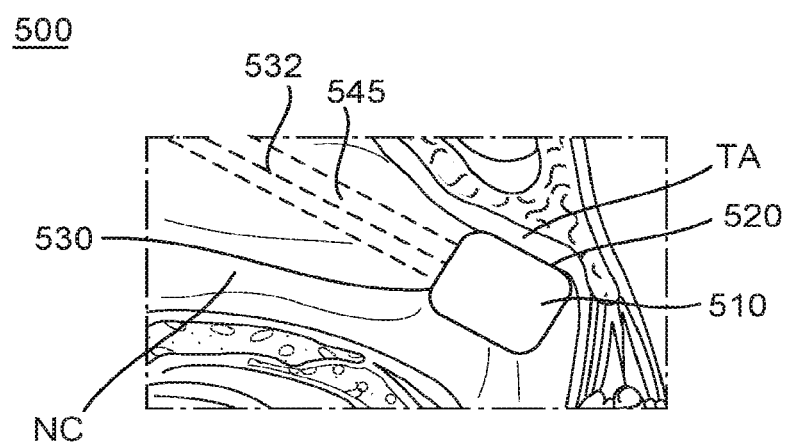

FIGS. 6A and 6B schematically illustrate a delivery system 500 according to a first embodiment. In this embodiment, delivery system 500 includes a reservoir 510 implemented as a unitary solid structure formed of a foam material. Therapeutic substance TS is disposed within the foam material of reservoir 510, and can move through the foam material to delivery interface 520, which is the distal surface of the foam structure.

In use, delivery interface 520 is placed in apposition with a target area TA to permit therapeutic substance TS to be absorbed into target area TA, such as by osmotic transport. In the embodiment depicted in FIGS. 6A and 6B, target area TA can be a subject's adenoid or tissue proximate to the adenoid. In other embodiments, target area TA can be another region in nasal cavity NC. Reservoir 510 can be filled, and/or refilled, with therapeutic substance TS, via inlet 530, which is the proximal surface of the foam structure.

Delivery system 500 can be deployed by inserting the foam structure into nasal cavity NC until delivery interface 520 is in apposition with target area TA. Optionally, delivery system 500 can include a retrieval element 545, coupled to reservoir 510, by which a user can remove delivery system 500 from nasal cavity NC of the subject by pulling delivery system 500 through nasal cavity NC.

Figure 7A:
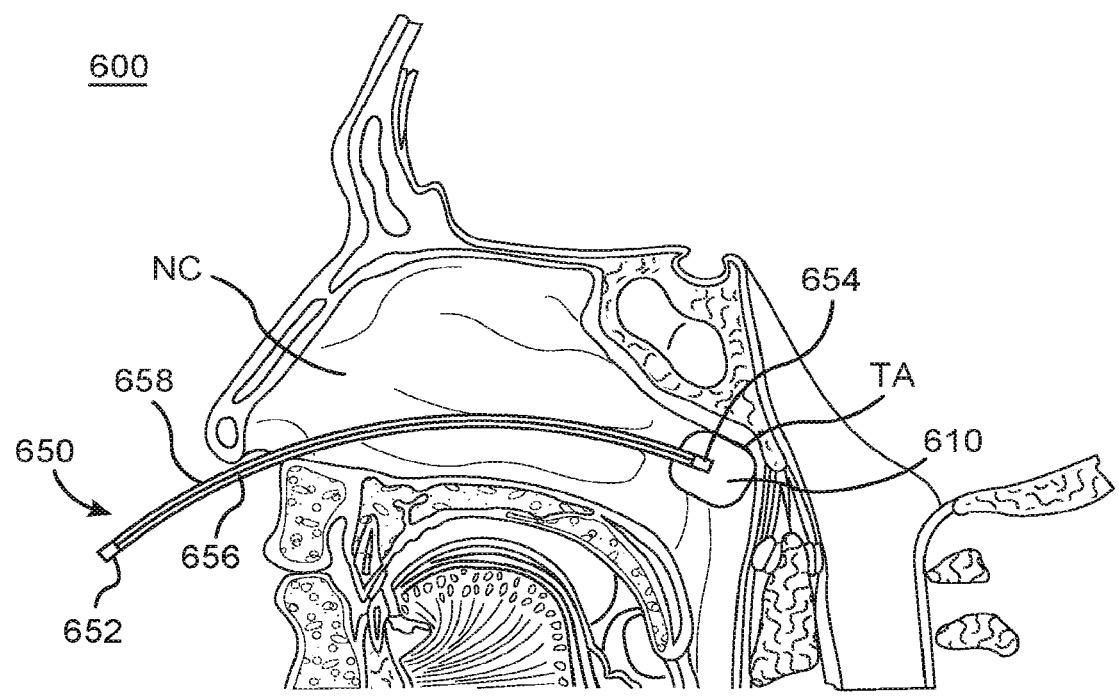
FIGS. 7A-7B are schematic illustrations of a therapeutic substance delivery system according to an embodiment.
Figure 7B:
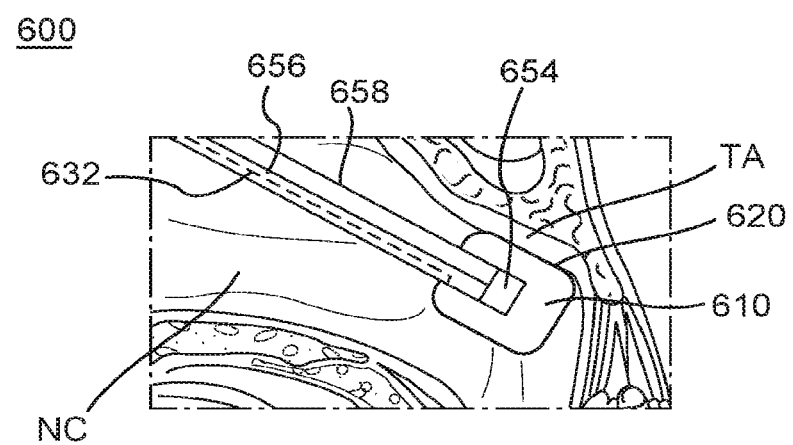

FIGS. 7A and 7B schematically illustrate a delivery system 600 according to another embodiment. Delivery system 600 can be similar to delivery system 500 but include an electrode device 650. For example, delivery system 600 includes a reservoir 610 implemented as a unitary solid structure formed of a foam material. An iontophoresis fluid IF containing a therapeutic substance can be disposed within the foam material of reservoir 610, e.g. the foam material of reservoir 610 can be saturated with iontophoresis fluid IF. The therapeutic substance within iontophoresis fluid IF can be transported via a delivery interface 620 (e.g., a distal surface of the foam structure) to a target area TA.

Delivery system 600 includes electrode device 650. Electrode device 650 can include an electrode tip 654, an elongate shaft 656, and a proximal connector 652. Electrode device 650 can also include a return electrode (not shown) that can be placed on the subject at a distance from electrode tip 654. Electrode tip 654 can be coupled to or separate from but engageable with reservoir 610. For example, electrode tip 654 can be coupled to reservoir 610 via a friction fit and/or an adhesive or other coupling mechanism. Electrode device 650 can be dimensioned such that it can be inserted into nasal cavity NC of the subject. In some embodiments, electrode device 650 can have smooth or rounded edges to reduce trauma to the subject as the electrode device 650 is inserted into nasal cavity NC. In some embodiments, electrode device 650 can be flexible. Electrode tip 654 can be constructed from a conductive material, such as, for example, a conductive metal. For example, electrode tip can be constructed from pure silver (e.g., 99.9% silver) and/or include a pure silver coating (e.g., a pure silver coating over a stainless steel electrode), which can provide reduced levels of electrolysis and changes in pH value when compared to other conductive materials such as, for example, stainless steel or gold. Electrode tip 654 can be disposed adjacent to an external surface of reservoir 610 or disposed within reservoir 610. Electrode tip 654 can have any general shape (e.g., cylindrical, rectangular, etc.).

In some embodiments, electrode tip 654 can have different configurations to increase surface area and promote iontophoresis. For example, electrode tip 654 can include one or more of: a plurality of wires configured similar to a brush head, a plurality of concentric tubes with staggered diameters that are nested within one another, a silver mesh mass configured similar to steel wool, a molded polymer matrix plug with a sponge-like structure and a metal plating or deposition (e.g., a pure silver plating or deposition), a metal-coated woven fabric, a honeycomb structure, a coil structure, a mass with a plurality of petals or branches (e.g., flower shaped), a flexible bag structure, one or more cavities or recesses with metal-coated surfaces, a textured surface (e.g., cross-hatched, etched, sandblasted), a laser-cut tube with cavities or recesses, etc. Electrode tip 654 can have a configuration that increases surface area but also minimizes a risk that a conductive region of electrode tip 654 comes into contact with tissue within nasal cavity NC. For example, electrode tip 654 can be formed of conductive and non-conductive regions, where the conductive regions are recessed within non-conductive regions and therefore prevented from coming into contact with a tissue surface within nasal cavity NC. Additionally or alternatively, electrode tip 654 can also be recessed within a non-conductive, insulating material (e.g., an outer sheath or sleeve) such that electrode tip 654 does not come into contact with a tissue surface. In some embodiments, electrode tip 654 can be attached to and disposed within reservoir 610 before being inserted into nasal cavity NC. Reservoir 610 can then prevent electrode tip 654 from directly contacting tissue within nasal cavity NC. In other embodiments, electrode device 650 can include a controller (not shown) that supplies power to electrode device 650 and controls when electrode device 650 applies a current to iontophoresis fluid IF. The controller can include safety features that prevent the electrode device 650 from activating and applying a current until the electrode device 650 is properly positioned within nasal cavity NC. For example, electrode device 650 can include a sensor that informs the controller of when electrode tip 654 of electrode device 650 is disposed within reservoir 610 before allowing a user to actuate the controller and apply an electric current.

In some embodiments, electrode tip 654 can include multiple metals with one metal (e.g., zinc) serving as a galvanic or sacrificial anode. In some embodiments, electrode device 650 can include a conveyor system (e.g., a flexible belt) that can be actuated to supply a fresh electrode surface during an iontophoresis procedure. In some embodiments, electrode device 650 can include wiping or cleaning mechanisms that can be actuated to clean the surface of electrode tip 654 to supply a new electrode surface. In some embodiments, electrode tip 654 can include a protective coating to help prevent corrosion.

Electrode tip 654 may be attached to the elongate shaft 656, e.g. by soldering or welding or by using a conductive adhesive. Elongate shaft 656 can be constructed from a conductive material. In some embodiments, elongate shaft 656 can be constructed from the same material as electrode tip 654. Elongate shaft 656 can be disposed within an outer sheath or sleeve 658. Outer sheath 658 can be formed of a non-conductive, insulating material. In some embodiments, portions of electrode device 650 (e.g., elongate shaft 656, outer sheath 658, or portions thereof) can be flexible or malleable such that a user can pre-shape electrode device 650 before inserting it into nasal cavity NC. Elongate shaft 656 can be attached to proximal connector 652, which can be electrically connected to a source for providing energy to electrode device 650. In other embodiments, electrode device 650 can be wirelessly energized, e.g. using a magnetic field that can induce an electric current in one or more coils disposed on electrode device 650.

Electrode device 650 can optionally include a fluid delivery channel 632 configured to supply iontophoresis fluid IF to reservoir 610. Fluid delivery channel 632 can be used to fill or refill reservoir 610 with iontophoresis fluid IF, as needed. In the embodiment shown in FIG. 7B, fluid delivery channel 632 is integrally formed in outer sheath 658. In other embodiments, fluid delivery channel 632 can be formed separately from outer sheath 658 but be coupleable (e.g., via an adhesive or other attachment mechanism) to outer sheath 658 and/or elongate shaft 656.

In operation, reservoir 610 and electrode device 650 can be deployed in nasal cavity NC. In some embodiments, electrode device 650 can be coupled to reservoir 610 (e.g., electrode tip 654 can be coupled to reservoir 610) and be used to deploy reservoir 610 into an operative position in nasal cavity (e.g., into operative apposition with target area TA). In other embodiments, reservoir 610 can be deployed in nasal cavity NC, e.g., via a deployment device, after which electrode device 650 can be inserted into nasal cavity NC and brought into engagement with reservoir 610. In other embodiments, electrode device 650 can be inserted into nasal cavity NC such that electrode tip 654 is disposed proximate to target area TA, after which reservoir 610 can be deployed in nasal cavity NC in operative apposition with TA and in engagement with electrode tip 654 of electrode device 650. Electrode device 650 can be used to perform an iontophoresis procedure to deliver the therapeutic substance to target area TA. As needed, additional iontophoresis fluid IF and/or therapeutic substance can be added to reservoir 610 by supplying it, e.g. via fluid delivery channel 632, to reservoir 610. After an iontophoresis procedure is performed, reservoir 610 and electrode device 650 can be removed from nasal cavity NC. In some embodiments, electrode device 650 can be coupled to reservoir 610, and a user can grasp a proximal end of electrode device 650 disposed outside of nasal cavity NC to remove the electrode device 650 and reservoir 610 from the nasal cavity. In other embodiments, electrode device 650 can be removed from nasal cavity NC (e.g., by a user grasping the proximal end of electrode device 650) and a retrieval element (not shown) coupled to reservoir 610 can be used to remove reservoir 610 from nasal cavity NC.

In addition or alternatively, reservoir 610 can include a fluid with non-ionic molecules that can be delivered to target area TA via electroosmosis. Electrode device 650 can be used to apply an electric current to a porous material, a capillary tube, or other fluid channel to induce the delivery of the non-ionic molecules through the fluid channel to target area TA.

Figure 8A:
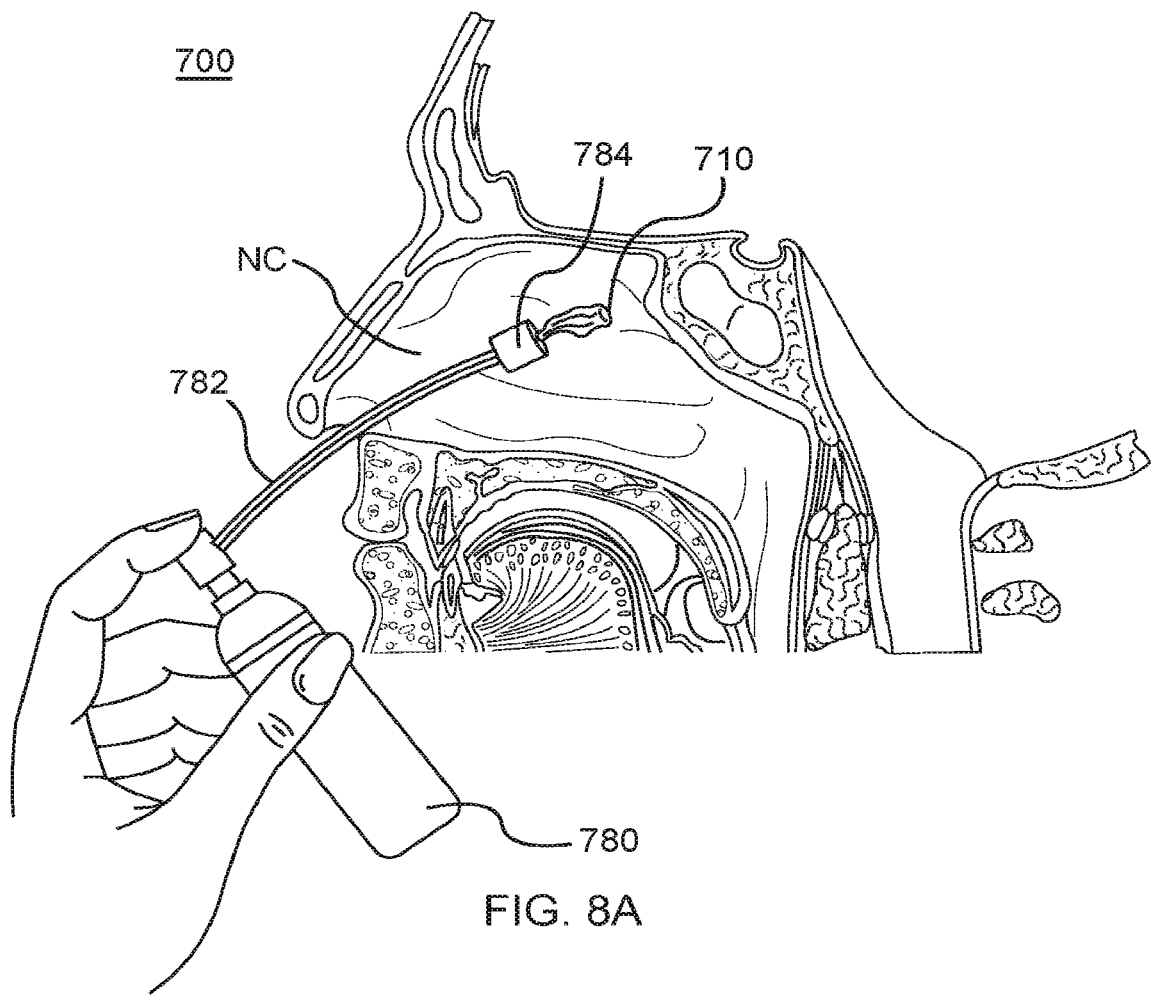
FIGS. 8A-8B are schematic illustrations of a therapeutic substance delivery system according to an embodiment.
Figure 8B:
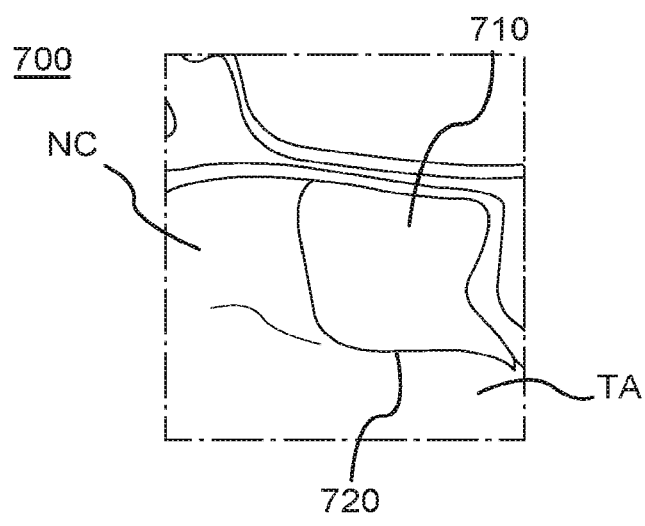

FIGS. 8A and 8B schematically illustrate a delivery system 700 according to another embodiment. In this embodiment, delivery system 700 includes a reservoir 710 disposed within nasal cavity NC. In this embodiment, reservoir 710 is formed in situ by injecting from a deployment device 780 a foamable carrier, or foam forming agent, mixed with therapeutic substance TS through nasal cavity NC into a region adjacent to target area TA. As best depicted in FIG. 8B, target area TA can be a region of a subject's superior turbinate, which can become inflamed due to infection, allergies, or other nasal conditions. In other embodiments, target area TA can be another region in nasal cavity NC. The foam-based reservoir 710 enables delivery of therapeutic substance TS to target area TA as the foam evaporates over time. The foam may also dissipate without leaving any residue, stains, or odor. The foam also provides a relatively uniform concentration of therapeutic substance TS at the surface of reservoir 710, such as at the delivery interface 720. The foam (or mousse) can be a lightweight material in cellular form that is made by introducing gas bubbles into a liquid phase. The carrier, or foam forming agent, can include foam producing agents and compounds that are able to generate a foamable composition when mixed with a liquid or gel composition. The foamable composition can generate a foam within deployment device 780 or upon dispensing from deployment device 780.

Deployment device 780 can have an elongate shaft 782. The elongate shaft 782 can be malleable or have a portion that is malleable such that the elongate shaft 782 can be configured to deliver reservoir 710 to a specific region of nasal cavity NC (e.g., a region adjacent to target area TA). For example, a user can configure (e.g., bend, shape, adjust) elongate shaft 782 such that a dispensing end 784 of deployment device 780 can be positioned in a specific region of nasal cavity NC, such as depicted in FIG. 7A, when deployment device 780 is inserted into nasal cavity NC. Elongate shaft 782 and dispensing end 784 can have rounded edges and/or have a soft or compressible external layer to reduce patient discomfort.

Suitable carrier compositions and techniques for delivering the foam are disclosed in U.S. Pat. No. 8,030,362 to Eliat, entitled "Compositions for Treatment of Ear Disorders and Methods of Use Thereof," and in U.S. Patent Application Publication No. 2015/0342965 to Lozinsky et al, entitled "Foamable Otic Pharmaceutical Compositions," the disclosures of which are incorporated herein by reference. An exemplary, suitable formulation for a foamable composition can include: (a) an oil-in-water emulsion that includes (i) the therapeutic agent in an effective concentration or amount, for example lidocaine in a 4% concentration solution; (ii) water in an amount of, for example, 75% or more (w/w), (iii) mineral oil in an amount of, for example, 15% or less (w/w); (iv) a synthetic surfactant pharmaceutically acceptable for nasal applications; (v) a foaming agent; and (vi) white petrolatum; and (b) a compressed propellant gas.

Figure 9:
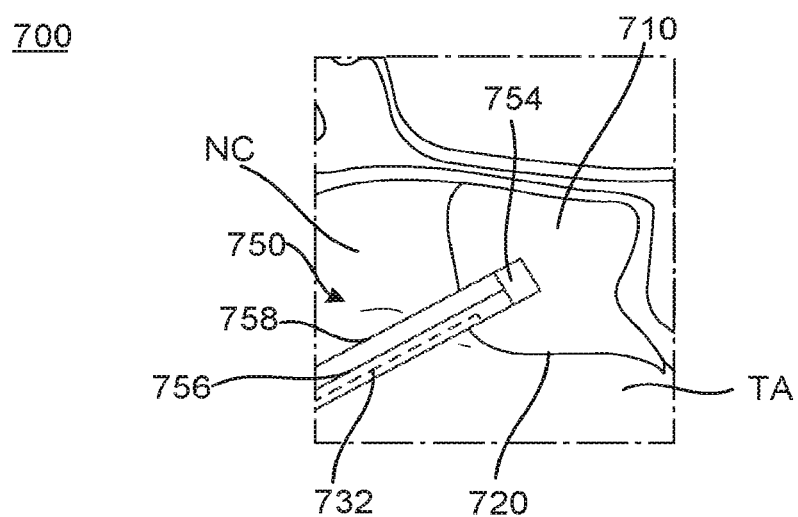
FIG. 9 is a schematic illustration of a therapeutic substance delivery system according to an embodiment.

In some embodiments, an electrode device 750 can be used to deliver a therapeutic substance to target area TA with delivery system 700, as schematically illustrated in FIG. 9. Reservoir 710 can include a foamable carrier mixed with iontophoresis fluid IF containing a therapeutic substance. For example, reservoir 710 can include a foamable composition (e.g., a liquid oil mixture) with an electrically charged therapeutic substance, such as, for example, lidocaine. Electrode device 750 can be similar to electrode device 650. For example, electrode device 750 can have an electrode tip 754, an elongate shaft 756, a proximal connector (not shown), an outer sleeve 758, and a return electrode (not shown). Optionally, electrode device 750 can also have a delivery channel 732, which can be used to deliver iontophoresis fluid IF and/or foam including iontophoresis fluid IF into nasal cavity NC.

In operation, deployment device 780 can be used to dispense reservoir 710 in an operative position within nasal cavity (e.g., in apposition with target area TA), and electrode device 750 can be inserted into nasal cavity NC such that electrode tip 754 of electrode device 750 is operatively engaged with reservoir 710, e.g. disposed in foam-based reservoir 710. Electrode device 750 can then supply an electric current to drive therapeutic substance within iontophoresis fluid IF into target area TA. After an effective dose of therapeutic substance has been delivered to target area TA, electrode device 750 can be removed from nasal cavity NC. Reservoir 710 can also be removed from nasal cavity NC or, alternatively, reservoir 710 can be left in nasal cavity NC to dissipate. In other embodiments, electrode device 750 can be inserted into nasal cavity NC such that its distal end is proximate to target area TA, and delivery channel 732 can be used to deliver foam including iontophoresis fluid IF into nasal cavity NC to form reservoir 710. After sufficient foam has been delivered into nasal cavity NC and a surface (e.g., delivery interface 720) is in operative apposition with target area TA, electrode device 750 can supply an electric current to deliver the therapeutic substance to target TA. Once an effective dose of therapeutic substance has been delivered, electrode device 750 can be removed from nasal cavity NC.

In addition or alternatively, reservoir 710 can include a fluid with non-ionic molecules that can be delivered to target area TA via electroosmosis similar to other delivery systems described herein.

Figure 10A:
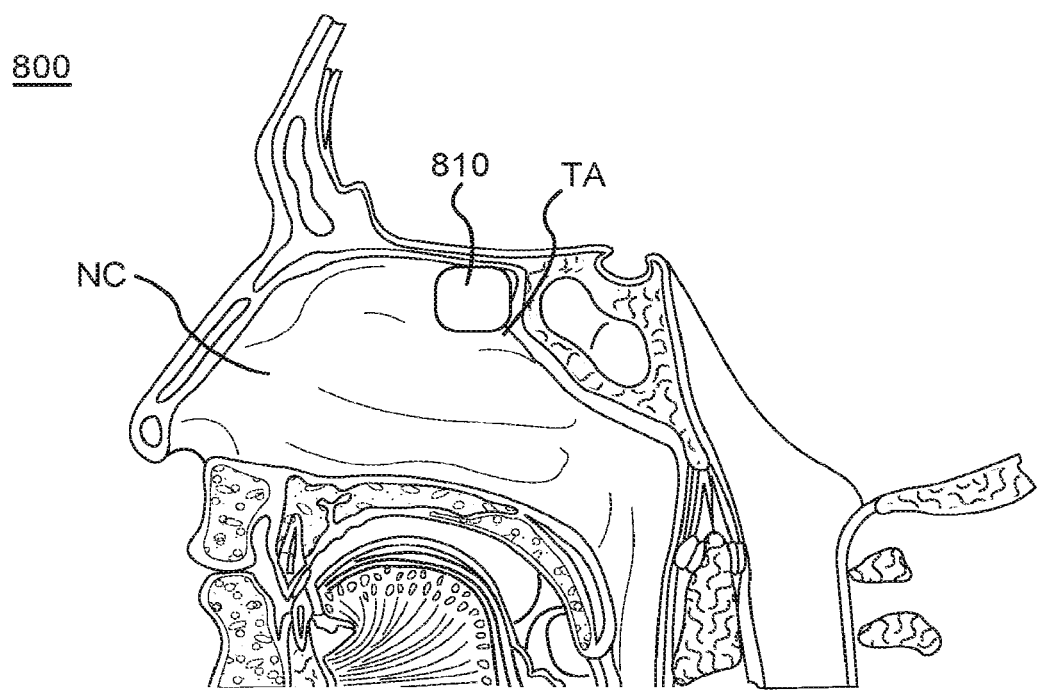
FIGS. 10A and 10B are schematic illustrations of a therapeutic substance delivery system according to an embodiment.
Figure 10B:
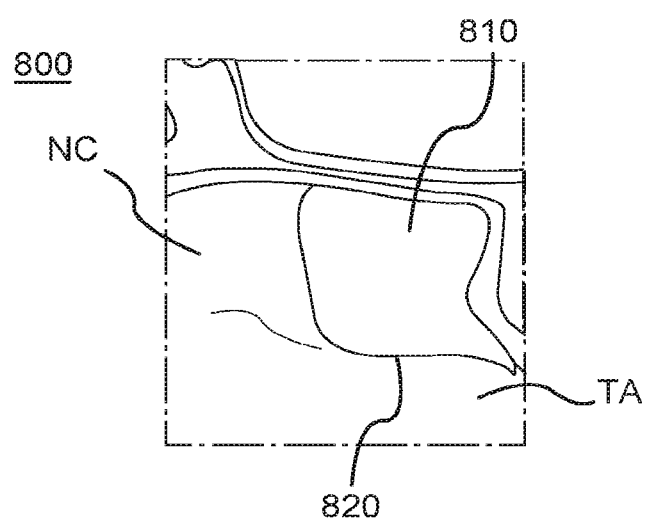

FIGS. 10A and 10B schematically illustrate a delivery system 800 according to another embodiment. Delivery system 800 is similar to delivery system 700, except that reservoir 810 can be formed in situ by injecting from a suitable deployment device (not shown) a hydrogel mixed with therapeutic substance TS through nasal cavity NC into the region adjacent to target area TA. The hydrogel-based reservoir 810 enables delivery of therapeutic substance TS to target area TA by osmotic transport and/or an iontophoresis procedure, as further described below.

A variety of hydrogel compositions may be suitable for delivery of different compositions of therapeutic substance TS. For example, photopolymerizable hydrogels disclosed in U.S. Pat. No. 5,410,016 to Hubbell et al, entitled "Photopolymerizable biodegradable hydrogels as tissue contacting materials and controlled-release carriers," the disclosure of which is incorporated herein by reference may be used. The method of use may include mixing the therapeutic substance TS with an aqueous solution including a light-sensitive free-radical polymerization initiator and a macromer to form a coating mixture. The coating mixture can be applied to target area TA (by any suitable means, such as a syringe) and then exposed to light sufficient to polymerize the macromer.

In other embodiments, the compositions and methods described in U.S. Pat. No. 6,201,065 to Pathak, et al., entitled "Multiblock biodegradable hydrogels for drug delivery and tissue treatment," the disclosure of which is incorporated herein by reference, may be used. In these embodiments, macromers may be crosslinked reversibly or irreversibly to form gels for controlled delivery of therapeutic substance TS. The composition and properties of the macromers can be selected and fabricated to produce hydrogels with desired delivery properties. The therapeutic substance TS may be provided in the macromer solution prior to or after administration, and either before or after gel formation, depending on the macromer composition. For example, the gels can be designed to have a selected rate of release of therapeutic substance TS, such as first order or zero order release kinetics. For specific therapeutic substances, such as peptides, the composition of the gel may be designed to result in pulsatile or mixed wave release characteristics in order to obtain maximum efficacy and to minimize side effects and tolerance development. The release profiles can be selected by the use of macromers and gels formed therefrom that respond to specific external stimuli such as ultrasound, temperature, pH or electric current. For example, the extent of swelling and size of these hydrogels can be modulated. Changes induced in the swelling directly correlate to the rate of release of the incorporated therapeutic substances. Through this, a particular release profile may be obtained. The hydrogels may be biodegradable so that removal is not required after administration or delivery. The gels permit controlled delivery and release of a biologically active therapeutic substance TS in a predictable and controlled manner locally at target area TA.

In other embodiments, rather than a hydrogel, reservoir 810 may be implemented with any non-Newtonian fluid that can be mixed with therapeutic substance TS and delivered through nasal cavity NC into the region adjacent to target area TA. That is, the material can flow under the shear forces produced by the delivery device, and then not flow under the lower shear forces imposed by gravity and normal movement of the subject, and thus can be retained in appropriate apposition with target area TA and deliver therapeutic substance TS, e.g. by osmotic transport and/or an iontophoresis procedure. Suitable materials may be shear thinning, i.e. apparent viscosity decreases with increased stress.

In other embodiments, rather than a hydrogel, reservoir 810 may be implemented with a fluid that can be mixed with therapeutic substance TS and delivered through nasal cavity NC into the region adjacent to target area TA and that can thicken, gel, or solidify in place. That is, the material can be delivered in liquid form (by any suitable device, such as a syringe, sprayer, etc.) and then be retained on target area TA and deliver therapeutic substance TS, e.g. by osmotic transport and/or an iontophoresis procedure. Suitable compositions can include those similar to compositions employed for "liquid bandages," e.g. polymers dissolved in solvents, which form a thin film when the solvent evaporates. Suitable polymers can include water-soluble polymers such as polyvinylpyrrolidone, alcohol-soluble polymers such as ethyl cellulose, pyroxylin/nitrocellulose, or poly(methactcrylate-isobutene-monoisopropylmaleate, and hexamethyldisoloxane- or isooctane-soluble polymers such as acrylate or siloxane.

In some embodiments, after hydrogel-based reservoir 810 is placed in operative apposition against target area TA, therapeutic substance TS within hydrogel-based reservoir 810 can be delivered to target area TA via diffusion (e.g., osmosis, perfusion, etc.). In other embodiments, after hydrogel-based reservoir 810 is placed in operative apposition against target area TA, an electrode device similar to electrode device 750 can be inserted into nasal cavity NC into operative engagement with reservoir 810. In these embodiments, reservoir 810 can include an iontophoresis fluid IF with the therapeutic substance, and the electrode device can be used to perform an iontophoresis procedure to deliver the therapeutic substance into target area TA, e.g. to supply an electric current that drives the therapeutic substance into target area TA. In other embodiments, hydrogel-based reservoir 810 can include non-ionic molecules that can be delivered to target area TA via electroosmosis similar to other delivery systems described herein. In some embodiments, therapeutic substance TS can be supplied to target area TA via both diffusion and an iontophoresis and/or electroosmosis procedure.

Figure 11A:
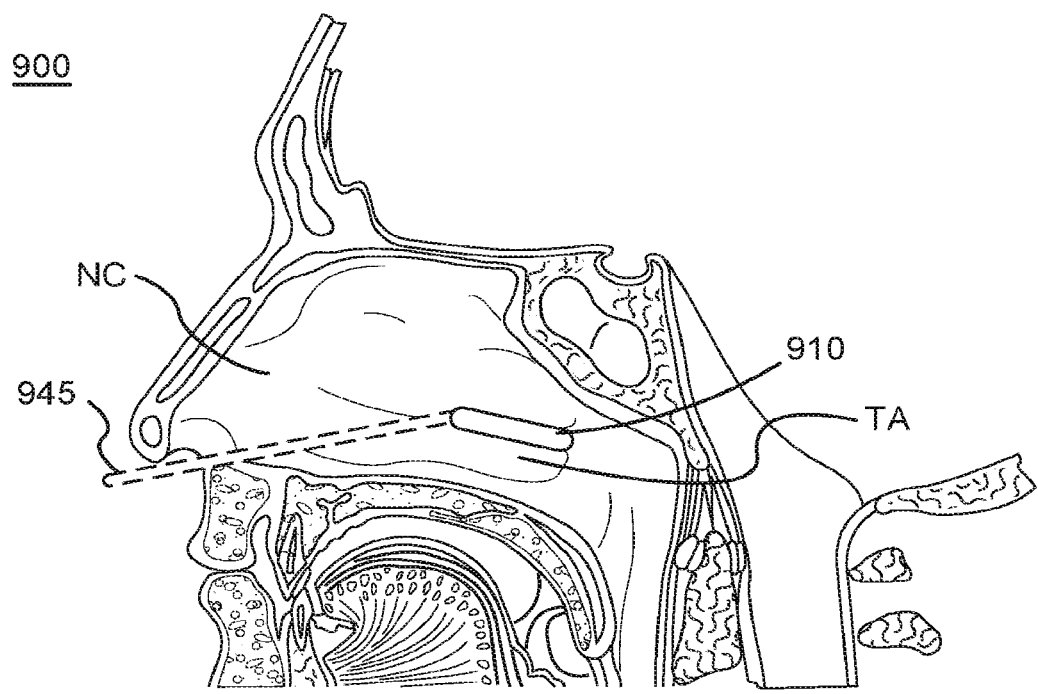
FIGS. 11A and 11B are schematic illustrations of a therapeutic substance delivery system according to an embodiment.

FIG. 11A schematically illustrates a delivery system 900 according to another embodiment. Delivery system 900 includes a reservoir 910 implemented as stable, solid, relatively thin film that may contain therapeutic substance TS, and that may be delivered through nasal cavity NC and secured to target area TA. Reservoir 910 can thus can be retained in appropriate apposition with target area TA and deliver therapeutic substance TS, e.g. by osmotic transport and/or an iontophoresis procedure. As depicted in FIG. 11A, target area TA can be a region of a subject's inferior turbinate, which can become inflamed due to infection, allergies, or another nasal condition. In other embodiments, target area TA can be another region in nasal cavity NC. Delivery system 900 may optionally include a retrieval element 945, such as a long tab, that is secured at its distal end to reservoir 910 and that can extend to a proximal end near or outside of the entrance to nasal cavity NC where it can be grasped by a user to retrieve reservoir 910 after the therapeutically effective amount of therapeutic substance TS has been delivered to target area TA.

Figure 11B:
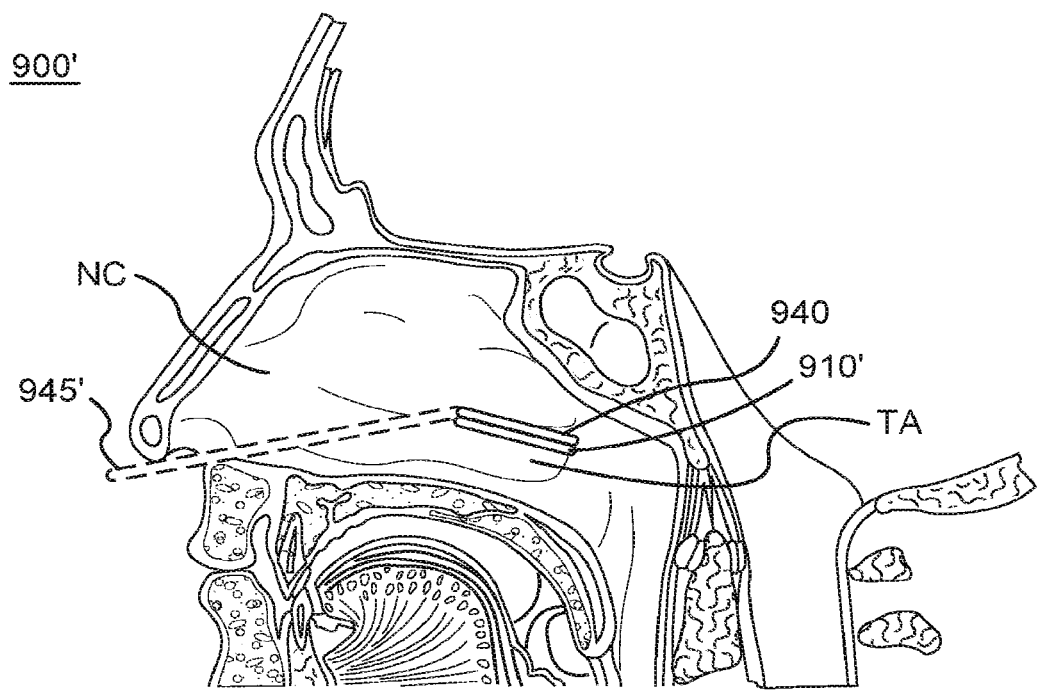

In another embodiment, shown in FIG. 11B, a delivery system 900' can include a stable, relatively thin film that is devoid of therapeutic substance, and instead form a body or substrate 940 supporting a reservoir 910'. In this embodiment, reservoir 910' can be a thin layer of any suitable material, including those discussed above, that can contain therapeutic substance TS. Similar to delivery system 900, delivery system 900' may optionally include a retrieval element 945', such as a long tab, that is secured at its distal end to the thin film body 940.

Figure 12A:
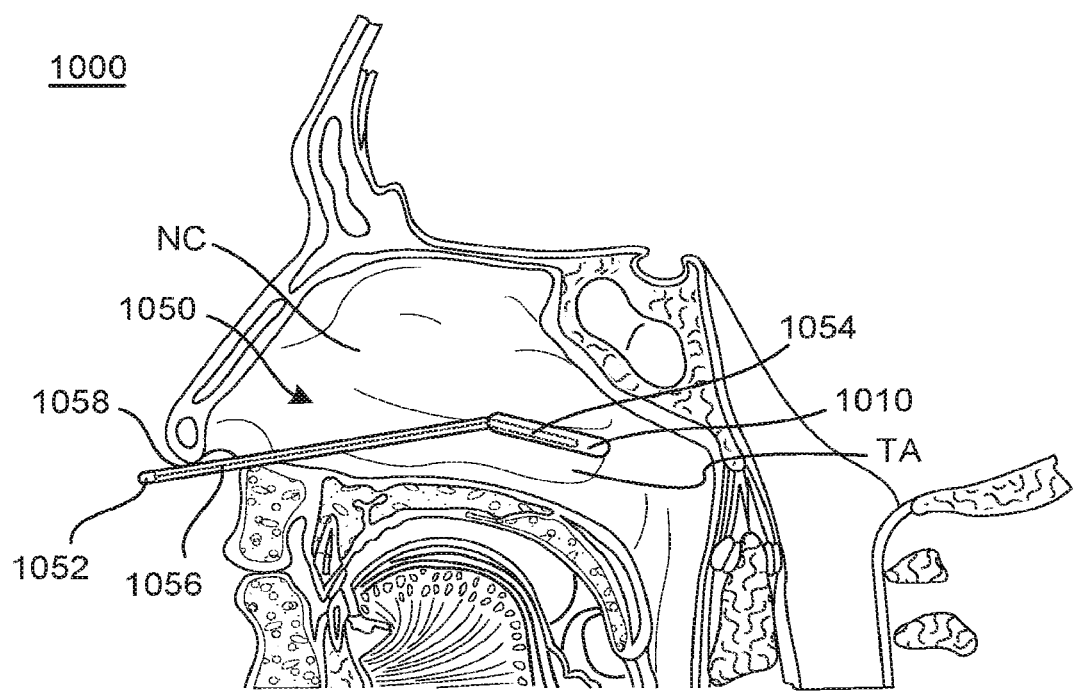
FIGS. 12A and 12B are schematic illustrations of a therapeutic substance delivery system according to an embodiment.
Figure 12B:
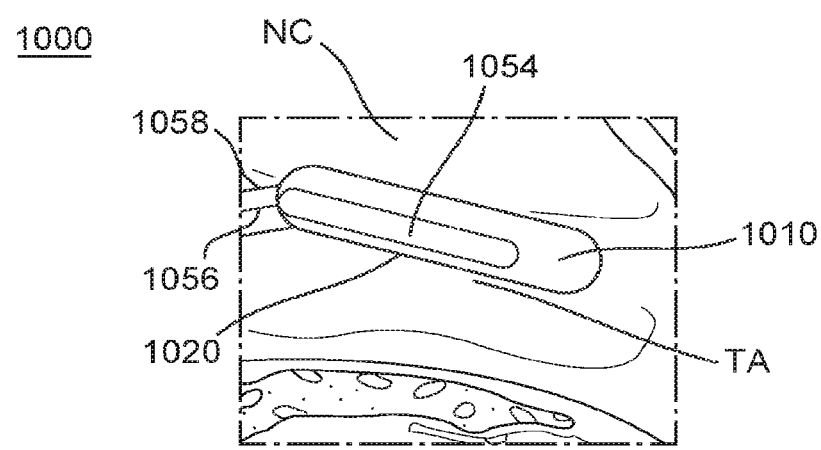

FIGS. 12A and 12B schematically illustrate a delivery system 1000 according to another embodiment. Similar to delivery systems 900 and 900', delivery system 1000 can include a reservoir 1010 implemented as a stable, solid, relatively thin film. Delivery system 1000 also includes an electrode device 1050 with a proximal connector 1052, an elongate shaft 1056, and an electrode 1054. Reservoir 1010 can support electrode 1054, which can be configured as a thin plate or pad. Reservoir 1010 can include an iontophoresis fluid IF, e.g. reservoir 1010 can be formed of a composition including a stable gel-based carrier and iontophoresis fluid IF or, alternatively, reservoir 1010 can be formed of a stable porous material that can hold iontophoresis fluid IF.

Electrode device 1050 can be similar to other electrode devices described herein. For example, elongate shaft 1056 of electrode device 1050 can be connected at its distal end to electrode 1054 and at its proximal end to proximal connector 1052. Electrode device 1050 can include a return electrode (not shown) that can be placed on the subject at a distance from electrode 1054. Elongate shaft 1056 and electrode 1054 can be constructed from conductive materials, such as, for example, one or more of a conductive metal, a conductive polymer, etc. Proximal connector 1052 can be electrically connected to a source for providing energy to electrode device 1050. In other embodiments, electrode device 1050 can be wirelessly energized, e.g. using a magnetic field that can induce an electric current in one or more coils disposed on electrode device 1050. Elongate shaft 1056 can be disposed within an outer sheath 1058, which can be formed of an insulating, non-conductive material. In some embodiments, portions of electrode device 1050 (e.g., elongate shaft 1056, outer sheath 1058, or portions thereof) can be flexible or malleable such that it can be adjusted by a user into multiple configurations (e.g., a straight configuration, a curved configuration, etc.). In particular, a user can adjust a portion of electrode device 1050 such that a distal end of electrode device 1050 (i.e., an end of electrode device 1050 with electrode 1054) can be positioned within nasal cavity NC in an operative location (e.g., an area adjacent to target area TA).

In operation, reservoir 1010 and electrode 1056 can be positioned proximate to target area TA such that a delivery interface 1020 is in operative apposition with target area. Proximal connector 1052 of electrode device 1050 can be connected to an energy source, and electrode device 1050 can be supplied with energy to perform an iontophoresis procedure. In particular, electrode device 1050, via electrode shaft 1056 and electrode 1054, can supply an electric current to reservoir 1010 to drive a therapeutic substance within iontophoresis fluid IF into target area TA. After an effective dose of therapeutic substance has been supplied to target area TA, electrode device 1050 and reservoir 1010 can be removed from nasal cavity NC.

In addition or alternatively, reservoir 1010 can include a fluid with non-ionic molecules that can be delivered to target area TA via electroosmosis similar to other delivery systems described herein.

Figure 13:
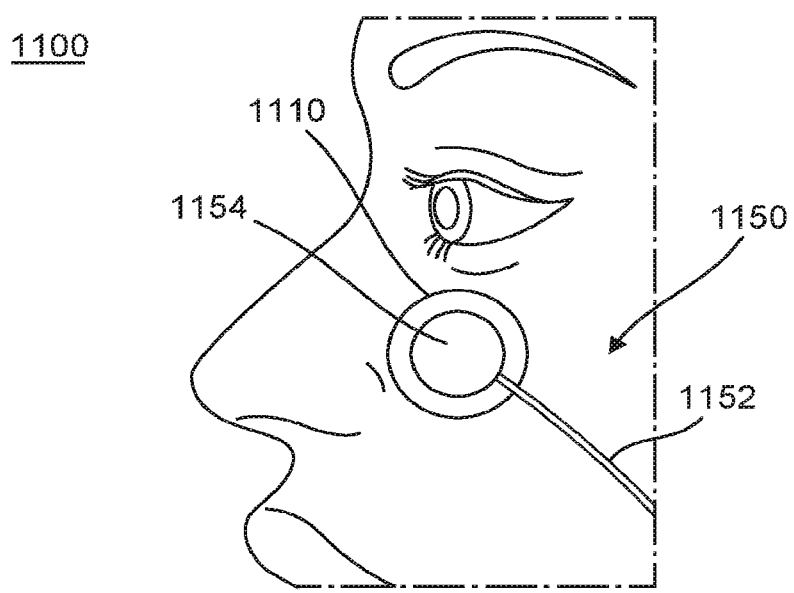
FIG. 13 is a schematic illustration of a therapeutic substance delivery system according to an embodiment.

FIG. 13 schematically illustrates a delivery system 1100 according to another embodiment. Delivery system 1100 includes a reservoir 1110 implemented as stable, solid, relatively thin film that may contain an iontophoresis fluid IF with a therapeutic substance. Similar to delivery system 1010, delivery system 1100 also includes an electrode device 1150 with an electrode 1154 formed as a thin plate or pad. Electrode 1154 can be supported on reservoir 1110. Electrode device 1150 also includes a shaft 1152 that is connected at its distal end to electrode 1154. Electrode device 1150 can be configured to supply an electric current to reservoir 1110 to perform an iontophoresis procedure. Delivery system 1100 can be positioned outside of a subject's nasal cavity NC. For example, as depicted in FIG. 13, delivery system 1100 can be positioned on skin adjacent to a subject's nose. Delivery system 1100 can be used to supply a therapeutic substance to a target area TA within or proximate to nasal cavity NC by delivering the therapeutic substance through the skin. In operation, reservoir 1110 and electrode 1154 can be secured to the subject's skin, and the electrode device 1150 can be used to supply an electric current to the reservoir 1110 to drive the therapeutic substance within iontophoresis fluid IF into and through the skin tissue to a target area TA beneath the skin. Additionally or alternatively, in some embodiments, electrode device 1150 can be used to supply an electric current to the reservoir 1110 to induce delivery of non-ionic molecules within a fluid into and through skin tissue. Since delivery system 1100 is not inserted into nasal cavity NC, delivery system 1100 is not restricted in size or shape by the anatomy of nasal cavity NC or the passageways or openings into nasal cavity NC (e.g., nostril openings or nasal nares). Thus, delivery system 1100 can have components that are dimensioned and configured differently from other delivery systems described herein. For example, electrode 1154 can be larger in size and have an increased surface area for promoting iontophoresis. Reservoir 1110 can have a larger delivery interface (e.g., delivery interface 320) for delivering therapeutic substance to a larger target area TA. Delivery system 1100 may also reduce patient discomfort by being disposed outside of nasal cavity NC.

Figure 14:
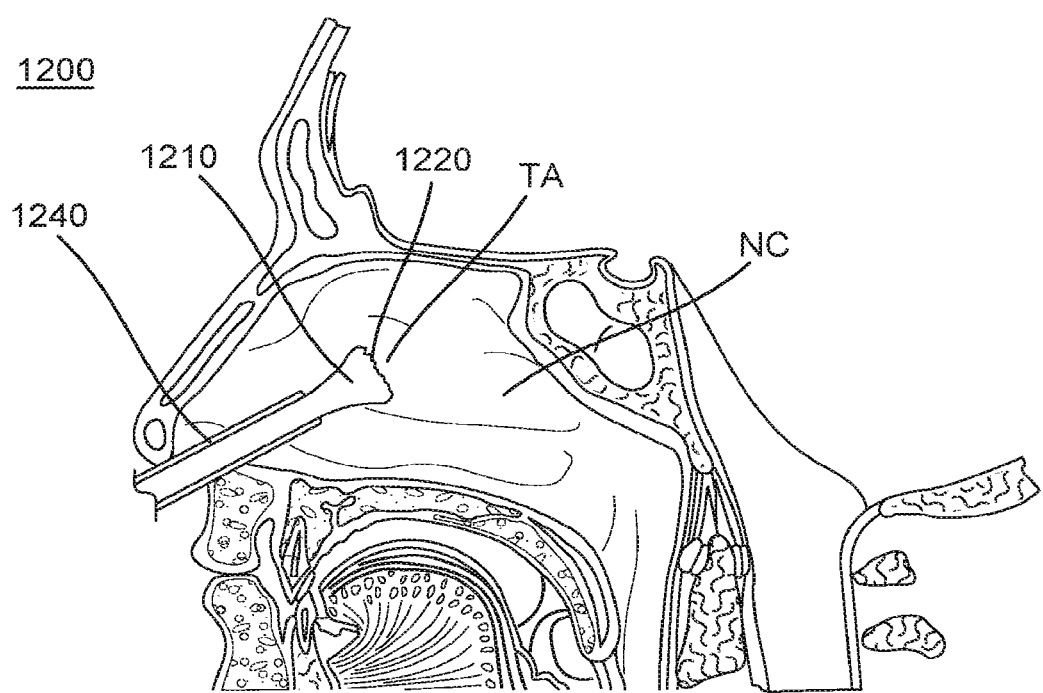
FIG. 14 is a schematic illustration of a therapeutic substance delivery system according to an embodiment.

FIG. 14 schematically illustrates a delivery system 1200 according to another embodiment. In this embodiment, reservoir 1210 is implemented as a bundle or other mass of wicking, fibrous material, i.e. a material that can absorb therapeutic substance TS in liquid form, and conduct therapeutic substance TS by capillary action through the body of reservoir 1210 to a distal surface of reservoir 1210, defining a delivery interface 1220, in operative apposition with target area TA, from which therapeutic substance TS can be delivered to target area TA by osmotic transport. In this embodiment, target area TA can be a region of a subject's middle turbinate, which can become inflamed due to infection, allergies, or other nasal conditions. In other embodiments, target area TA can be another region within nasal cavity NC. Delivery system 1200 may include a body 1240, such as a tube of material, that radially constrains the fibrous material and increases its stiffness to facilitate insertion through nasal cavity NC. As needed, therapeutic substance TS can be added to reservoir 1210 by supplying, or resupplying, it, e.g. in liquid form, to a proximal surface or end of the wicking material, serving as an inlet.

Figure 15:
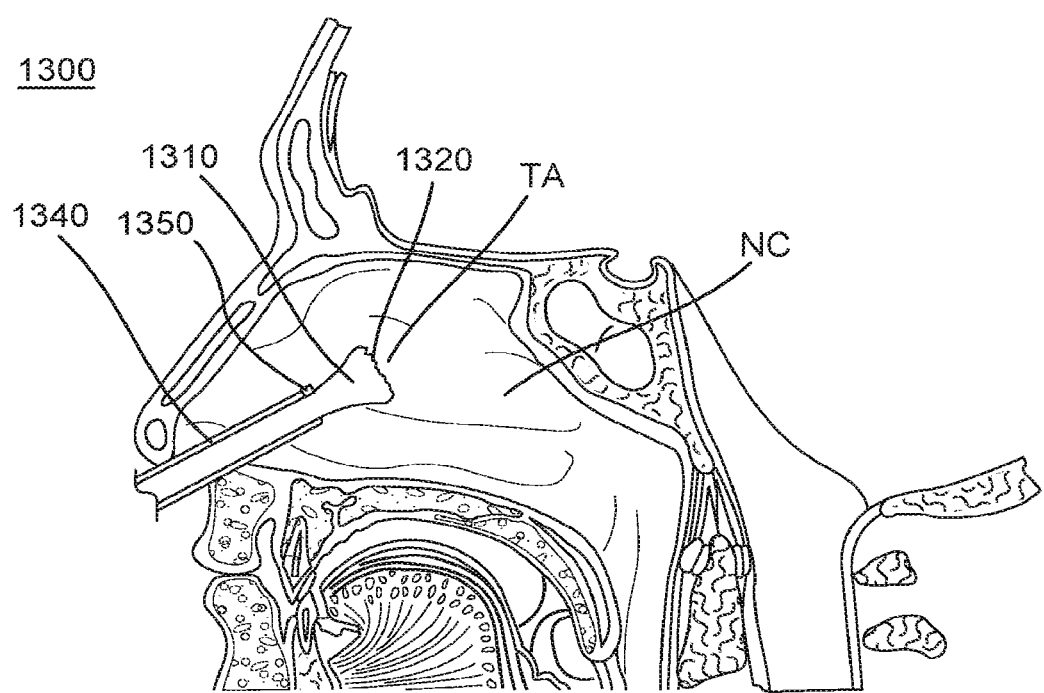
FIG. 15 is a schematic illustration of a therapeutic substance delivery system according to an embodiment.

FIG. 15 schematically illustrates a delivery system 1300 according to another embodiment. Similar to delivery system 1200, delivery system 1300 can include a reservoir 1310 that is implemented as a bundle or other mass of wicking, fibrous material. Reservoir 1310 can absorb an iontophoresis fluid IF containing therapeutic substance and conduct iontophoresis fluid IF by capillary action through body of reservoir 1310 to a distal surface of reservoir 1310, defining a delivery interface 1320, in operative apposition with target area TA. As needed, iontophoresis fluid IF and/or therapeutic substance can be added to reservoir 1310 by supplying, or resupplying, it, e.g. in liquid form, to a proximal surface or end of the wicking material, serving as an inlet.

Delivery system 1300 also includes a body 1340, such as a tube of material, that radially constrains the fibrous material and increases its stiffness to facilitate insertion through nasal cavity NC. Body 1340 can support an electrode device 1350, which can be engaged with reservoir 1310 and be used to deliver an electric current to reservoir 1310. Electrode device 1350 can be supplied with energy, e.g. via a wired connection and/or wirelessly. For example, electrode device 1350 can be connected to an energy source via a wire (not shown) that is supported on body 1340. Additionally or alternatively, electrode device 1350 can include a harvesting coil that can be wirelessly energized using a magnetic field.

In addition or alternatively, reservoir 1310 can include a fluid with non-ionic molecules that can be delivered to target area TA via electroosmosis similar to other delivery systems described herein.

Figure 16:
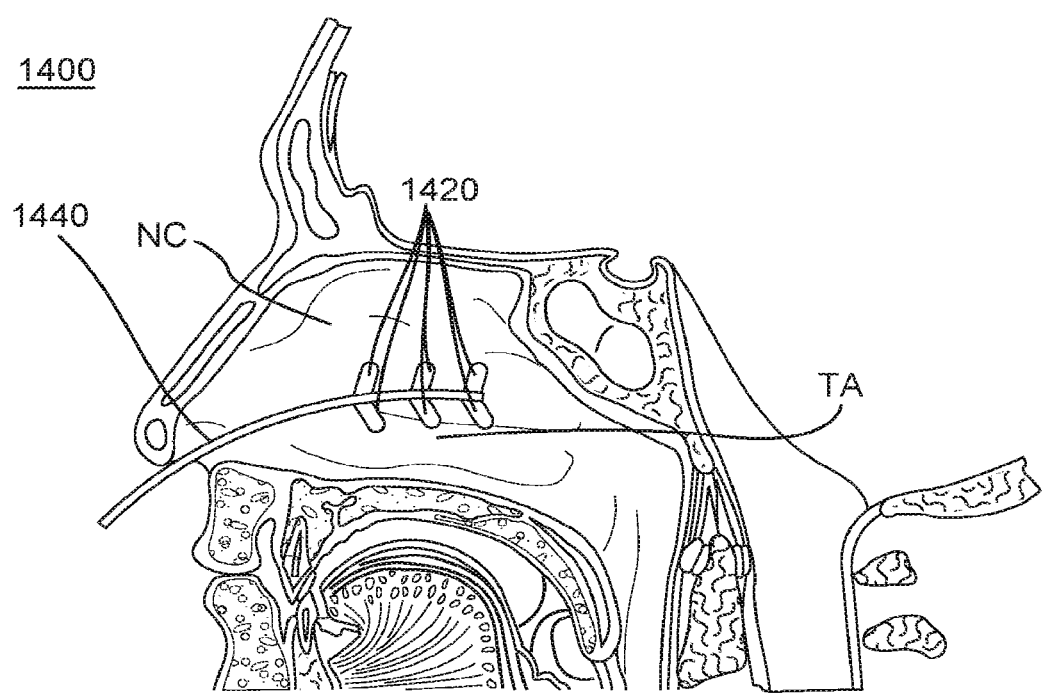
FIG. 16 is a schematic illustration of a therapeutic substance delivery system according to an embodiment.

FIG. 16 schematically illustrates a delivery system 1400 according to another embodiment. Delivery system 1400 can be similar to other delivery systems described herein but include a plurality of reservoirs 1420. Reservoirs 1420 can be implemented as, for example, a foam, a hydrogel, a thin film, a fibrous material, or other material containing therapeutic substance TS. Reservoirs 1420 can be implemented in the same form, or some of reservoirs 1420 can be implemented in a first form (e.g., a foam) and others of reservoirs 1420 can be implemented in a second form (e.g., a hydrogel). Reservoirs 1420 can be supported on a body 1440. In the embodiment shown in FIG. 16, reservoirs 1420 are supported on body 1440 spaced from one another, but in other embodiments, reservoirs 1420 can be disposed adjacent to one another. Reservoir 1420 can provide increased surface area and multiple delivery interfaces such that therapeutic substance TS can be delivered to a larger target area TA and/or multiple target areas TA.

Figure 17:
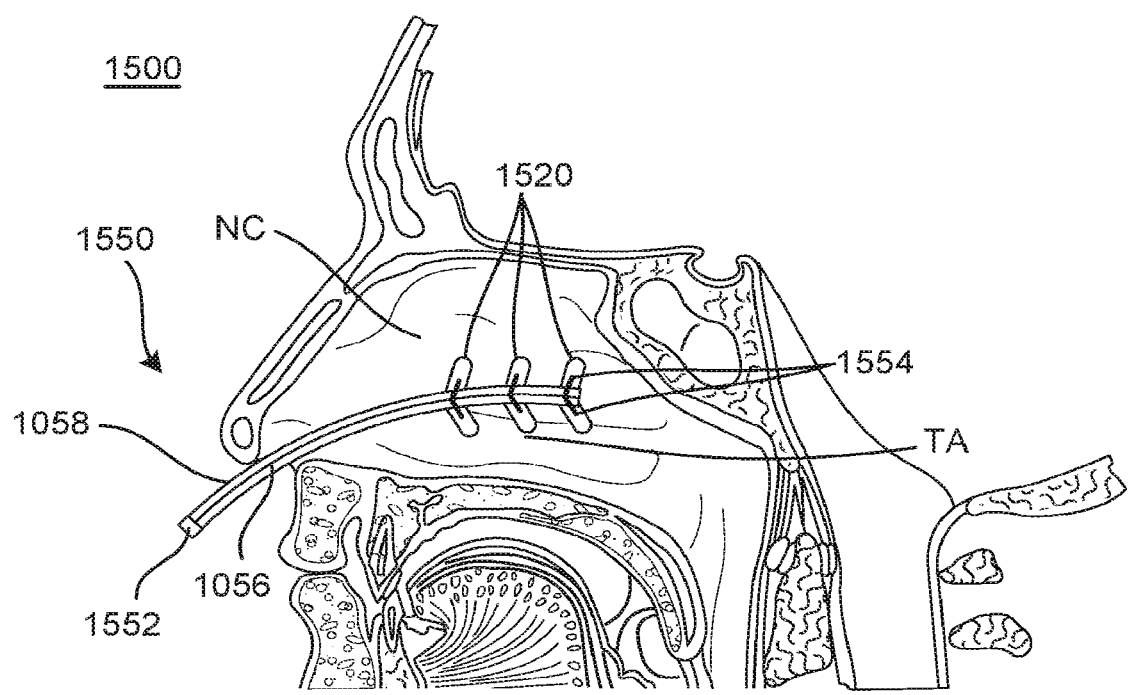
FIG. 17 is a schematic illustration of a therapeutic substance delivery system according to an embodiment.

FIG. 17 schematically illustrates a delivery system 1500 according to another embodiment. Similar to delivery system 1400, delivery system 1500 can include a plurality of reservoirs 1520. Reservoirs 1520 can be implemented as, for example, a foam, a hydrogel, a thin film, a fibrous material, or other material containing iontophoresis fluid IF with a therapeutic substance. Reservoirs 1520 can be implemented in the same form, or some of reservoirs 1520 can be implemented in a first form (e.g., a foam) and others of reservoirs 1520 can be implemented in a second form (e.g., a hydrogel). Reservoir 1520 can provide increased surface area and multiple delivery interfaces such that the therapeutic substance can be delivered to a larger target area TA and/or multiple target areas TA.

Delivery system 1500 can include an electrode device 1550. Electrode device 1550 can be similar to other electrode devices described herein but include a plurality of electrodes 1554 for applying electric current to iontophoresis fluid IF. For example, electrode device 1550 can have a proximal connector 1552, an elongate shaft 1556, and an outer sheath 1558. Electrode device 1550 can also include a return electrode (not shown) that is disposed on the subject at a distance from the plurality of electrodes 1554, e.g., on the subject's neck, shoulder, etc. Elongate shaft 1556 and electrodes 1554 can be formed of a conductive material, e.g. stainless steel and/or silver. Elongate shaft 1556 can be disposed within outer sheath 1558, which can be formed of an insulating, non-conductive material. Proximal connector 1552 can connect to a source for supplying energy to electrode device 1550. Each of electrodes 1554 can be operatively engaged with a reservoir 1520. Thus, electrodes 1554 can supply an electrical current to reservoirs 1520. As depicted in FIG. 17, electrodes 1554 and/or reservoirs 1520 can be supported on a distal portion of electrode device 1550 spaced apart from one another. In other embodiments, electrodes 1554 and/or reservoirs 1520 can be disposed adjacent to one another on electrode device 1550 and have different configurations (e.g., have different sizes, shapes, or structures). In some embodiments, elongate shaft 1556 and outer sheath 1558, or portions of elongate shaft 1556 and outer sheath 1558, can be flexible or malleable such that a user can configure electrode device 1550 to position electrodes 1554 and reservoirs 1520 in specific regions within nasal cavity NC.

In addition or alternatively, reservoirs 1520 can include a fluid with non-ionic molecules that can be delivered to target area TA via electroosmosis similar to other delivery systems described herein.

Figure 18A:
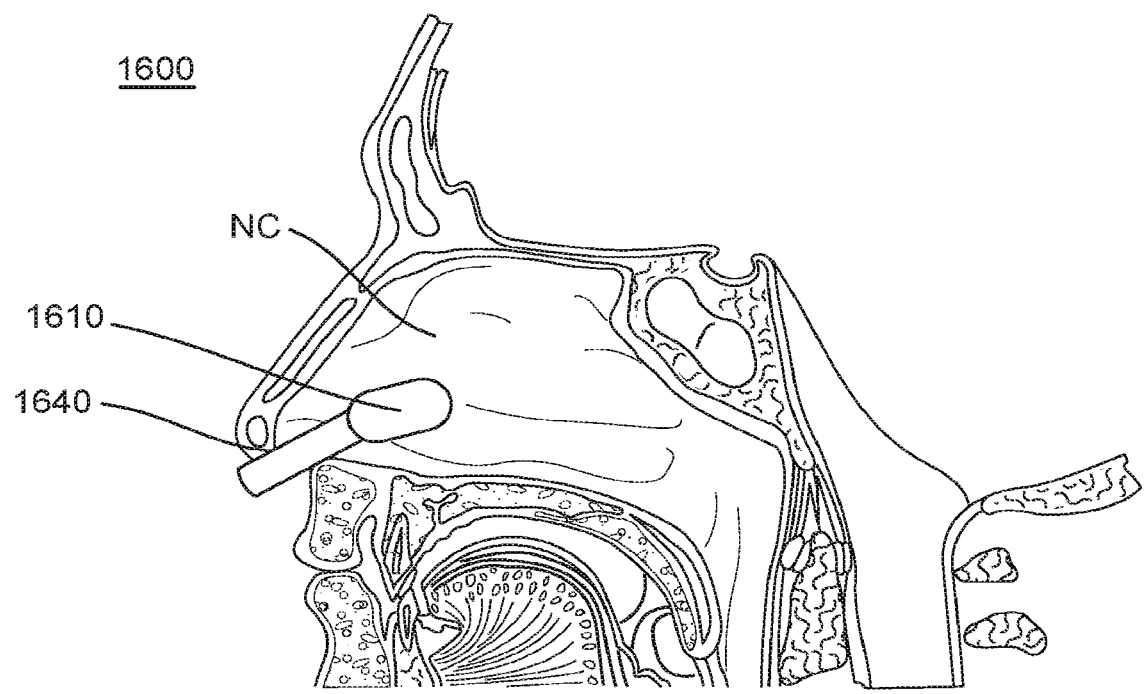
FIGS. 18A and 18B are schematic illustrations of a therapeutic substance delivery system according to an embodiment.
Figure 18B:
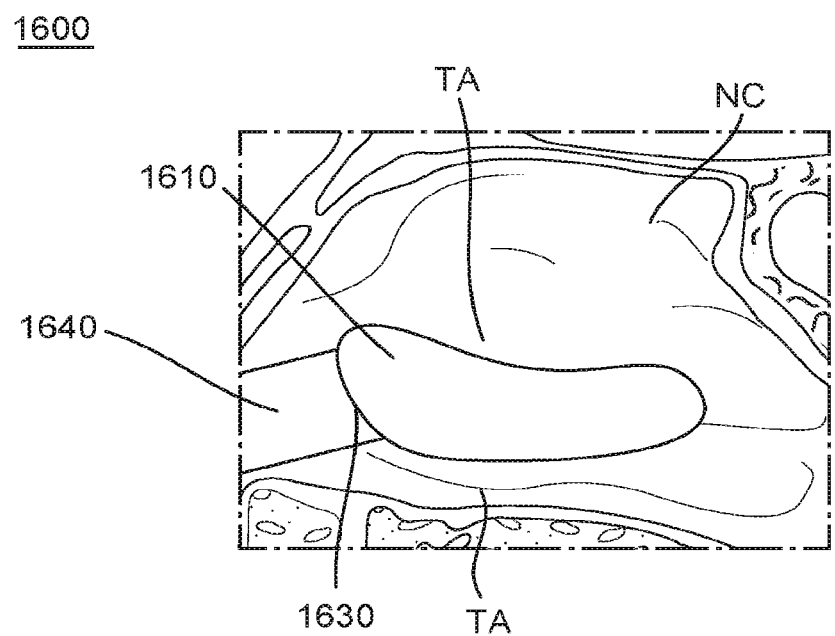

FIGS. 18A and 18B schematically illustrate a delivery system 1600 according to another embodiment. Delivery system 1600 is similar to other delivery systems described herein. Delivery system 1600 includes a body 1640 implemented as a nasal plug. The nasal plug can be inserted into a subject's nasal nares or nostrils. The nasal plug can prevent fluid discharge or the discharge of other material from the subject's nasal cavity NC. Body 1640 can support, define, and/or be coupled to a reservoir 1610 that can be implemented as a foam or other material (e.g., a liquid, a mousse, a hydrogel). In some embodiments, reservoir 1610 can be implemented as a solid material (e.g., a foam) that can change into a liquid once positioned within nasal cavity NC, e.g., due to a change in temperature. Reservoir 1610 can be configured to change shape (e.g., expand) once positioned within nasal cavity NC. In some embodiments, body 1640 and reservoir 1610 can be formed as a single integrated unit. For example, body 1640 and reservoir 1610 can be formed of a foam material that can be inserted into the subject's nostrils such that a portion of the material is disposed within nasal cavity NC. In other embodiments, body 1640 can be formed as a separate component (e.g., a plastic plug or stop, a packed fibrous material, etc.) on which reservoir 1610 can be supported.

Reservoir 1610 can expand to occupy the space within nasal cavity NC. For example, as depicted in FIG. 18B, reservoir 1610 can expand to fill the middle meatus and come into contact with anterior portions of the middle and inferior turbinates and a portion of the nasal wall. Reservoir 1610 can expand in response to changes in various conditions such as, for example, temperature, moisture level, etc. In some embodiments, reservoir 1610 can be positioned within nasal cavity NC, and a therapeutic substance TS such as a liquid can be added to reservoir 1610 via an inlet 1630 to cause reservoir 1610 to expand within nasal cavity NC. In other embodiments, reservoir 1610 can expand within nasal cavity NC in response to being positioned within nasal cavity NC, e.g., due to a temperature change.

Reservoir 1610 can contain a therapeutic substance TS and enable therapeutic substance TS to be eluted, diffused, or released by other mechanisms to one or more target areas TA within nasal cavity NC. For example, once reservoir 1610 has expanded within nasal cavity NC, as depicted in FIG. 18B, reservoir 1610 can enable therapeutic substance TS to diffuse into anterior portions of the middle and inferior turbinates. As needed, therapeutic substance TS may be added to reservoir 1610 by supplying it, e.g. in liquid form, to a proximal surface of reservoir 1610, serving as inlet 1630.

In some embodiments, reservoir 1610 can be implemented as a liquid containing therapeutic substance TS or a solid material that is configured to change into a liquid once positioned within nasal cavity NC. Body 1640, which is implemented as a nasal plug, can prevent the liquid from discharging from nasal cavity NC via the subject's nostrils. And the subject may lean forward or lie on the subject's stomach to contain the fluid within an anterior region of nasal cavity NC and to prevent it from draining out of nasal cavity NC via the throat.

Figure 19A:
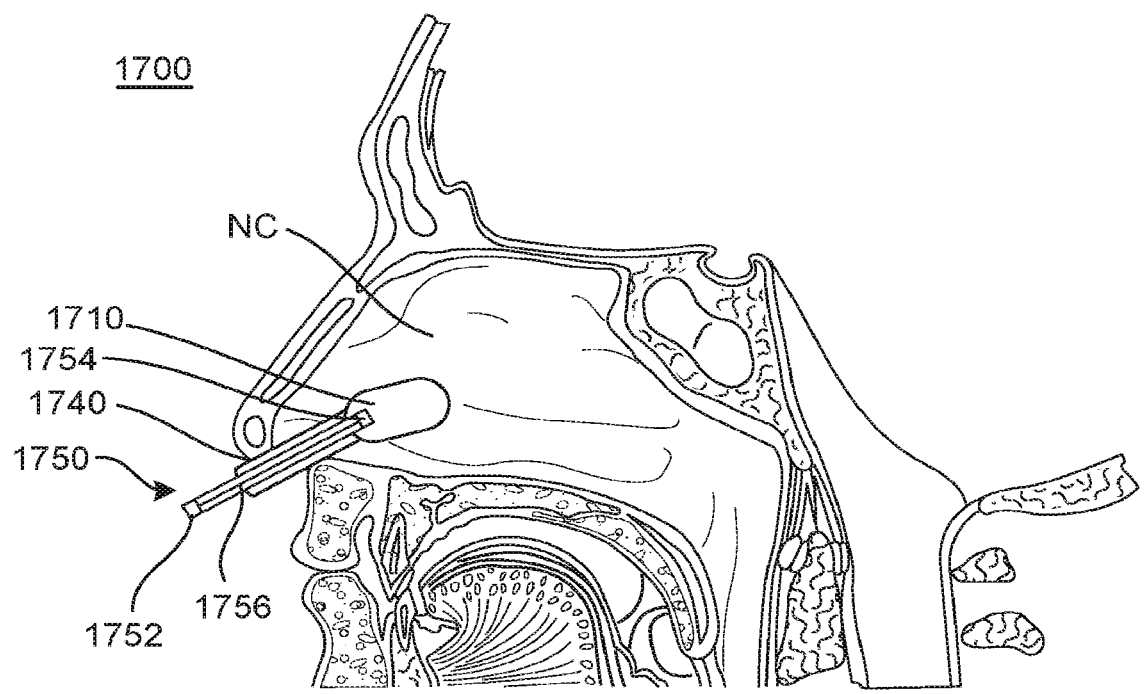
FIGS. 19A and 19B are schematic illustrations of a therapeutic substance delivery system according to an embodiment.
Figure 19B:
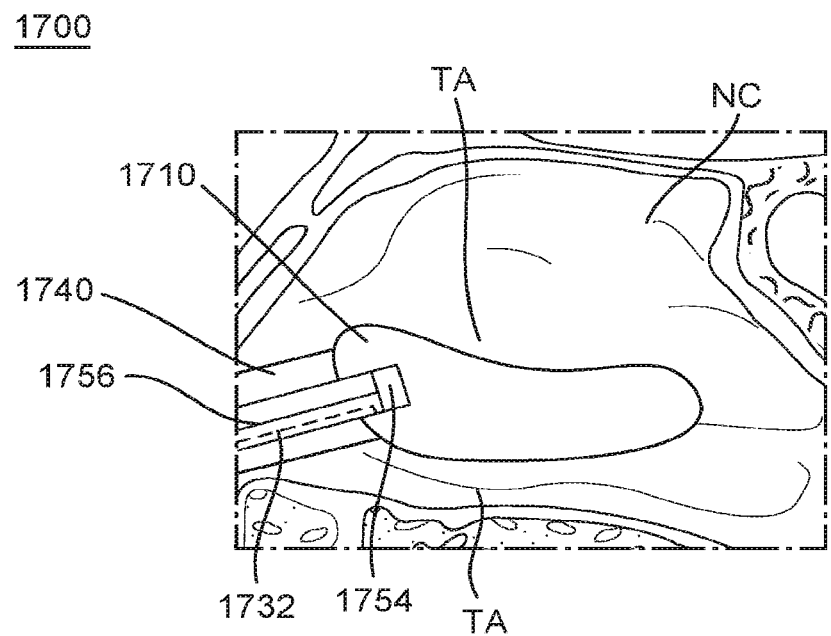

FIGS. 19A and 19B schematically illustrate a delivery system 1700 according to another embodiment. Delivery system 1700 can be similar to delivery system 1600 but include an electrode device 1750. For example, delivery system 1700 includes a body 1740 implemented as a nasal plug, and a reservoir 1710 implemented as a foam. An iontophoresis fluid IF containing a therapeutic substance can be disposed within the foam of reservoir 1710, e.g. the foam of reservoir 1710 can be saturated with iontophoresis fluid IF. The therapeutic substance within iontophoresis fluid IF can be driven via iontophoresis to one or more target areas TA.

Electrode device 1750 can be similar to other electrode devices described herein. For example, electrode device 1750 can include a conductive tip or electrode 1754, an elongate shaft 1756, and a proximal connector 1752. Electrode device 1750 also includes a return electrode (not shown) that can be placed on the subject at a distance from electrode 1754. Electrode device 1750 can be coupled to or separate from by engageable with body 1740 and reservoir 1710. Body 1740 can be designed to prevent conductive regions of electrode device 1750 (e.g., electrode 1754) from coming into direct contact with a tissue surface of the subject's nasal cavity NC. For example, body 1740 can form an enclosure or surrounding around a portion of electrode device 1750 such that electrode 1754 and/or other conductive regions of electrode device 1750 are spaced from the nasal wall and other tissue surfaces within nasal cavity NC.

Electrode 1754 can be disposed within reservoir 1710 such that electrode 1754 can deliver an electric current to reservoir 1710 in order to deliver the therapeutic substance within iontophoresis fluid IF into target areas TA. Optionally, electrode device 1750 can also have a delivery channel 1732, which can be used to deliver iontophoresis fluid IF and/or foam including iontophoresis fluid IF into nasal cavity NC.

In addition or alternatively, reservoir 1710 can include a fluid with non-ionic molecules that can be delivered to target area TA via electroosmosis similar to other delivery systems described herein.

Conclusion

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An apparatus comprising:
   (a) a reservoir structure containing a volume of iontophoretic fluid and including a delivery interface configured to be placed in operative apposition with a first side of a tissue surface within a nasal cavity of a subject and is configured to maintain at least some of the iontophoretic fluid in proximity to the first side of the tissue surface, wherein,
     (i) the iontophoretic fluid is an ionic solution including ions of a therapeutic substance, and
     (ii) the therapeutic substance is selected from a group consisting of analgesics, anesthetics, anti-inflammatories, antibiotics, antivirals, antifungals, antiparasitics, decongestants, mucokinetics, antihistamines, antioxidants, immunosuppressive agents, dissociatives, steroids, sedatives, hypnotics, anticholinergics, antiemetics, antiepiletics, and combinations thereof,
     (iii) the reservoir structure comprises at least one of a sponge, a foam, a mousse, a hydrogel, or a mass of fibrous material, wherein the at least one of the sponge, the foam, the mousse, the hydrogel, or the mass of fibrous material is an electrically conducting material; and
   (b) an electrode device including a proximal portion and a distal portion, wherein
     (i) the electrode device configured for the proximal portion to be disposed outside of the nasal cavity while the distal portion extends into the nasal cavity into engagement with a portion of the reservoir structure,
     (ii) the electrode device further configured to apply a current to the reservoir structure such that an amount of the ions of the therapeutic substance is delivered to a target area of the subject on a second side of the tissue surface, and
     (iii) the reservoir structure configured to maintain the delivery interface against the first side of the tissue surface for at least a first predefined period of time during which current is being applied by the electrode device to the structure.

2. The apparatus of claim 1, wherein the delivery interface of the reservoir structure is configured to conform to a shape of the first side of the tissue surface.

3. The apparatus of claim 1, wherein
   (a) the volume of iontophoretic fluid is a first volume of iontophoretic fluid, and
   (b) the reservoir structure is configured to receive a second volume of the iontophoretic fluid while maintaining the delivery interface against the first side of the tissue surface.

4. The apparatus of claim 1, wherein the electrode device is configured to apply the current according to a ramped current profile.

5. The apparatus of claim 1, wherein the therapeutic substance is an anesthetic.

6. The apparatus of claim 1, wherein the therapeutic substance is a steroid.

7. The apparatus of claim 6, wherein the steroid has a molecular weight between approximately 400 Da and approximately 500 Da.

8. The apparatus of claim 1, wherein the at least one of the sponge, the foam, the mousse, the hydrogel, or the mass of fibrous material is disengageably connected to the apparatus such that the at least one of the sponge, the foam, the mousse, the hydrogel, or the mass of fibrous material can be disengaged from the electrode device and maintained within the nasal cavity when the distal portion electrode device is withdrawn from the nasal cavity.

9. An apparatus comprising:
   (a) a reservoir structure containing a volume of iontophoretic fluid and including a delivery interface configured to be placed in operative apposition with a first side of a tissue surface within a nasal cavity of a subject and is configured to maintain at least some of the iontophoretic fluid in proximity to the first side of the tissue surface, wherein,
     (i) the reservoir structure configured to deform to increase an area of engagement between the delivery interface and the first side of the tissue surface, wherein
       (A) the reservoir structure comprises at least one of a sponge, a foam, a mousse, a hydrogel, or a mass of fibrous material, and
       (B) the at least one of the sponge, the foam, the mousse, the hydrogel, or the mass of fibrous material is an electrically conducting material,
     (ii) the iontophoretic fluid is an ionic solution including ions of a therapeutic substance, and
     (iii) the therapeutic substance is selected from a group consisting of analgesics, anesthetics, anti-inflammatories, antibiotics, antivirals, antifungals, antiparasitics, decongestants, mucokinetics, antihistamines, antioxidants, immunosuppressive agents, dissociatives, steroids, sedatives, hypnotics, anticholinergics, antiemetics, antiepiletics, and combinations thereof;
   (b) an electrode device including a portion of the electrode device configured to engage with a portion of the reservoir structure, wherein
     (i) the electrode device configured to apply a current to the reservoir structure such that an amount of the ions of the therapeutic substance is delivered to a target area of the subject on a second side of the tissue surface; and
   (c) a retrieval element configured to enable removal of the reservoir structure from the nasal cavity, wherein the retrieval element including
     (i) a distal portion coupled to the reservoir structure, and
     (ii) a proximal portion extending from within the nasal cavity to a location outside of the nasal cavity.

10. The apparatus of claim 9, wherein the reservoir structure includes at least one of the sponge or the hydrogel.

11. The apparatus of claim 9, wherein the delivery interface of the reservoir structure is configured to conform to a shape of the first side of the tissue surface.

12. The apparatus of claim 9, wherein
(a) the electrode device includes an exposed electrode disposed on the distal portion of the retrieval element, and
(b) the exposed electrode configured to deliver the current to the reservoir structure.

13. The apparatus of claim 9, wherein the electrode device is configured to apply the current according to a ramped current profile.

14. The apparatus of claim 9, wherein the therapeutic substance is an anesthetic.

15. The apparatus of claim 9, wherein the therapeutic substance is a steroid.

16. The apparatus of claim 15, wherein the steroid has a molecular weight between approximately 400 Da and approximately 500 Da.

17. A method comprising:
(a) disposing a delivery system including a delivery interface in a nasal cavity of a subject such that the delivery interface is in operative apposition with a first side of a tissue surface, wherein
  (i) the delivery system containing an iontophoretic solution including ions of a therapeutic substance,
  (ii) the therapeutic substance is selected from a group consisting of analgesics, anesthetics, anti-inflammatories, antibiotics, antivirals, antifungals, antiparasitics, decongestants, mucokinetics, antihistamines, antioxidants, immunosuppressive agents, dissociatives, steroids, sedatives, hypnotics, anticholinergics, antiemetics, antiepiletics, and combinations thereof; and
  (iii) the delivery system configured to change configuration to conform to shape of the first side of the tissue surface after being disposed in the nasal cavity, wherein
    (A) the delivery system comprises at least one of a sponge, a foam, a mousse, a hydrogel, or a mass of fibrous material, and
    (B) the at least one of the sponge, the foam, the mousse, the hydrogel, or the mass of fibrous material is an electrically conducting material;
(b) maintaining the delivery interface in operative apposition with the first side of the tissue surface for a predefined period of time; and
(c) applying, during the predefined period of time and using an electrode device, a current to the delivery system such that an amount of the ions of the therapeutic substance is delivered via the delivery interface to a target area of the subject on a second side the tissue surface.

18. The method of claim 17 further comprising:
(a) retrieving, after the applying the current to the delivery system, the delivery system from the nasal cavity using a retrieval element, wherein the retrieval element including
  (i) a distal portion coupled to the delivery interface, and
  (ii) a proximal portion extending from within the nasal cavity to a location outside of the nasal cavity.

19. The method of claim 17, wherein the therapeutic substance is an anesthetic.

20. The method of claim 17, wherein the therapeutic substance is a steroid.

21. The method of claim 20, wherein the steroid has a molecular weight between approximately 400 Da and approximately 500 Da.

* * * * *